(12) United States Patent
Gifford et al.

(10) Patent No.: US 11,180,796 B2
(45) Date of Patent: Nov. 23, 2021

(54) DETECTION OF MUTATIONS REGARDING ONE OR MORE DEOXYRIBONUCLEIC ACID SEQUENCES USING DETERMINISTIC LATERAL DISPLACEMENT ARRAYS

(71) Applicant: International Business Machines Corporation, Armonk, NY (US)

(72) Inventors: Stacey Gifford, Fairfield, CT (US); Benjamin Wunsch, Mt. Kisco, NY (US); Joshua T. Smith, Croton on Hudson, NY (US); Sung-Cheol Kim, New York, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 321 days.

(21) Appl. No.: 16/007,389

(22) Filed: Jun. 13, 2018

(65) Prior Publication Data

US 2019/0382821 A1    Dec. 19, 2019

(51) Int. Cl.
*C12Q 1/6827* (2018.01)
*C12Q 1/683* (2018.01)
*C12Q 1/6816* (2018.01)

(52) U.S. Cl.
CPC ............ *C12Q 1/683* (2013.01); *C12Q 1/6816* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,403,338 B1 * | 6/2002 | Knapp | B01L 3/502784 435/91.2 |
| 6,955,874 B2 | 10/2005 | Singh et al. | |
| 7,745,119 B2 | 6/2010 | Koshinsky et al. | |
| 7,906,287 B2 | 3/2011 | Dahlhauser | |
| 8,323,929 B2 | 12/2012 | Wang et al. | |

(Continued)

FOREIGN PATENT DOCUMENTS

| | | |
|---|---|---|
| CA | 2049429 A1 | 2/1992 |
| CN | 105019033 A | 11/2015 |

(Continued)

OTHER PUBLICATIONS

Gao et al , J. Mol. Recognit., vol. 30, article e2638, pp. 1-11, published online 2017.*

(Continued)

*Primary Examiner* — Robert T. Crow
(74) *Attorney, Agent, or Firm* — Amin, Turocy & Watson, LLP

(57) ABSTRACT

Techniques regarding screening for mutations using nanoscale deterministic arrays are provided. For example, one or more embodiments described herein can comprise a method, which can comprise cleaving a deoxyribonucleic acid segment hybridized with a molecular probe to form a sample fluid. The cleaving can occur at a first end and a second end of the molecular probe. Also, the cleaving can comprise a cleaving agent that targets base pair mismatches. The method can also comprise supplying the sample fluid to a nanoscale deterministic lateral displacement array to screen for a single nucleotide polymorphism.

13 Claims, 11 Drawing Sheets

(56) References Cited

U.S. PATENT DOCUMENTS

| | | |
|---|---|---|
| 8,796,506 B2 | 8/2014 | Gielen et al. |
| 8,975,216 B2 | 3/2015 | Rank et al. |
| 9,559,240 B1 | 1/2017 | Astier et al. |
| 10,253,350 B2 | 4/2019 | Gifford et al. |
| 2001/0014449 A1* | 8/2001 | Nerenberg ............. B82Y 10/00 435/6.17 |
| 2004/0072247 A1* | 4/2004 | Pfistershammer .......................... C12Q 2565/501 435/7.1 |
| 2008/0023399 A1 | 1/2008 | Inglis et al. |
| 2012/0220479 A1 | 8/2012 | Ericsson et al. |
| 2014/0155271 A1 | 6/2014 | Hatchwell et al. |
| 2015/0136601 A1 | 5/2015 | Austin et al. |
| 2015/0368706 A1 | 12/2015 | Cao et al. |
| 2016/0047735 A1 | 2/2016 | Grisham et al. |
| 2016/0146778 A1 | 5/2016 | Astier et al. |
| 2016/0320389 A1 | 11/2016 | Astier et al. |
| 2017/0035734 A1* | 2/2017 | Bray ...................... A61K 45/06 |
| 2017/0342477 A1 | 11/2017 | Jensen et al. |

FOREIGN PATENT DOCUMENTS

| | | |
|---|---|---|
| JP | 2007061080 A | 3/2007 |
| WO | 2011047359 A2 | 4/2011 |
| WO | 2013154770 A1 | 10/2013 |

OTHER PUBLICATIONS

Isono et al., Nuc. Acids Res., vol. 44, pp. 2977-2986, published online Mar. 21, 2016.*

Pimkin et al, BMC Biotech., vol. 7, Article 29, pp. 1-8, published 2007).*

Brow et al, Focus, vol. 18, pp. 2-5, published 1996.*

Grompe et al , Proc. Nat. Acad. Sci. USA, vol. 89, pp. 5888-5892, published Aug. 1989.*

Cotton et al, Proc. Nat. Acad. Sci. USA, vol. 85, pp. 4397-4401, published Jun. 1988.*

Kojima et al, PATAI's Chemistry of Functional Groups, pp. 1-45, published 2010.*

Smith, et al. "Microfluidic Chips With One or More Vias Filled With Sacrificial Plugs." U.S. Appl. No. 16/168,292, filed Oct. 23, 2018. 37 pages.

Inglis, et al. Critical particle size for fractionation by deterministic lateral displacement, Lab on a Chip, 2006, pp. 655-658, vol. 6.

Wunsch, et al., Nanoscale lateral displacement arrays for the separation of exosomes and colloids down to 20 nm, Nature Nanotechnology, Aug. 1, 2016, 7 Pages.

List of IBM Patents or Applications Treated as Related.

Non-Final Office Action received for U.S. Appl. No. 16/007,347 dated Aug. 19, 2020, 68 pages.

Final Office Action received for U.S. Appl. No. 16/007,347 dated Dec. 14, 2020, 43 pages.

Kaji et al., "Separation of Long DNA Molecules by Quartz NanopiUar Chips under a Direct Current Electric Field", Analytical Chemistry, vol. 76, No. 1, Jan. 1, 2004, pp. 15-22.

Non-Final Office Action received for U.S. Appl. No. 16/007,347 dated May 6, 2021, 15 pages.

* cited by examiner

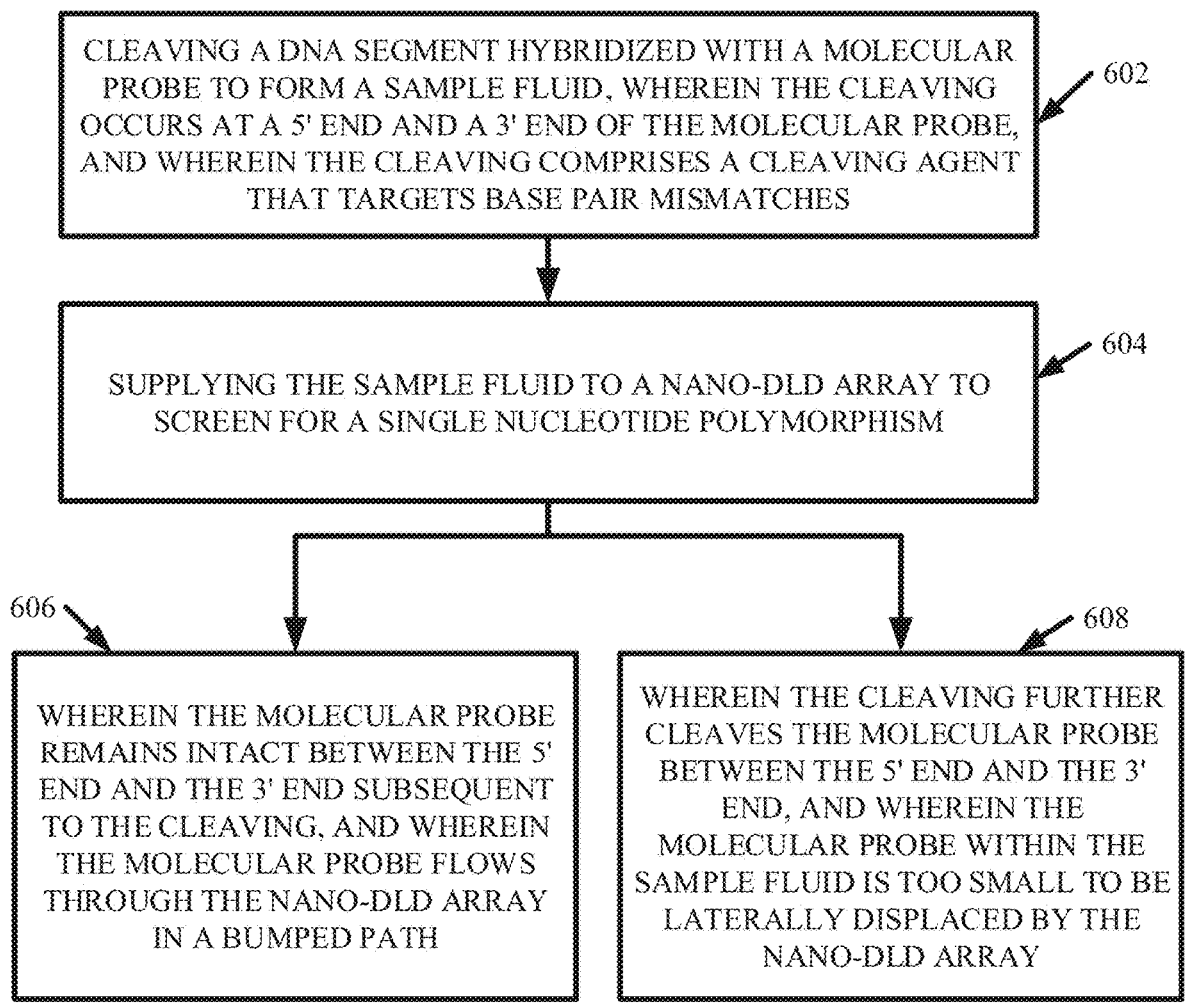

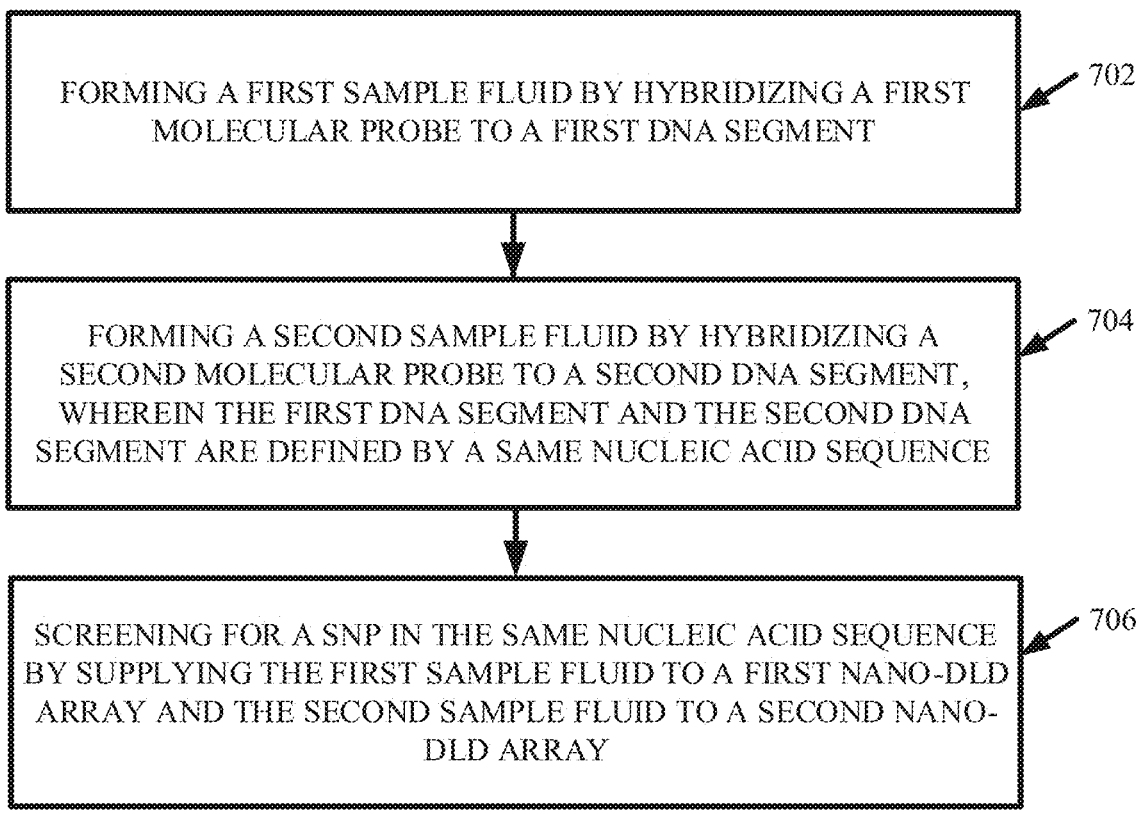

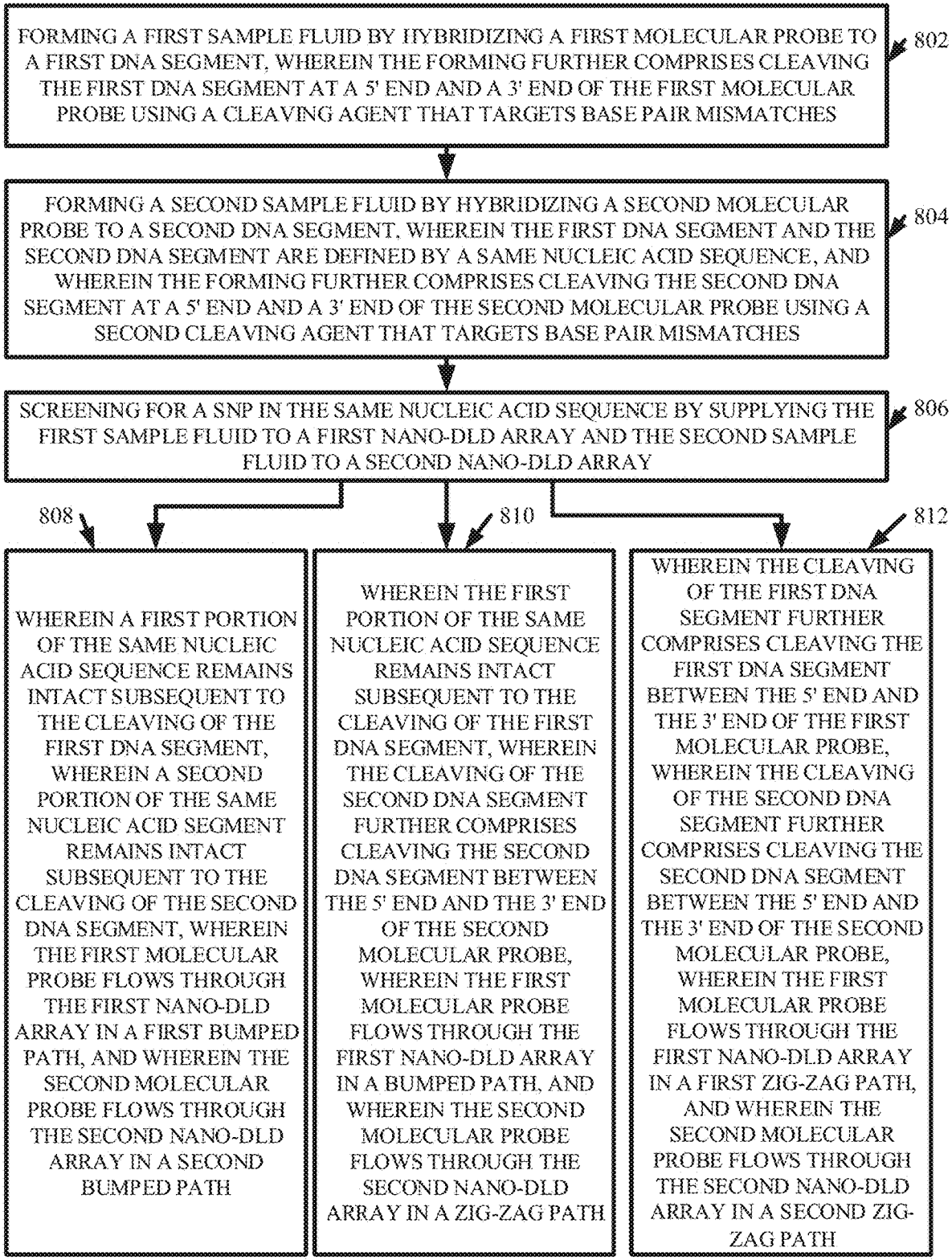

```
┌─────────────────────────────────────────────────────────┐
│ ADDING A FIRST MOLECULAR PROBE TO A SAMPLE OF GENETIC   │ ◂— 902
│ MATERIAL, WHEREIN THE FIRST MOLECULAR PROBE HAS AN      │
│ AFFINITY TO BOND TO A TARGET NUCLEIC ACID SEQUENCE      │
└─────────────────────────────────────────────────────────┘
                            │
                            ▼
┌─────────────────────────────────────────────────────────┐
│ HYBRIDIZING A SECOND MOLECULAR PROBE TO A REFERENCE     │ ◂— 904
│ NUCLEIC ACID SEQUENCE COMPRISED WITHIN THE SAMPLE OF    │
│ GENETIC MATERIAL                                        │
└─────────────────────────────────────────────────────────┘
                            │
                            ▼
┌─────────────────────────────────────────────────────────┐
│ SCREENING FOR A MUTATION IN THE SAMPLE OF GENETIC       │
│ MATERIAL BY SUPPLING THE SAMPLE OF GENETIC MATERIAL     │ ◂— 906
│ TO A NANO-DLD ARRAY, WHEREIN THE FIRST MOLECULAR        │
│ PROBE IS SMALLER THAN A CRITICAL DIAMETER FOR LATERAL   │
│ DISPLACEMENT BY THE NANO-DLD ARRAY                      │
└─────────────────────────────────────────────────────────┘
```

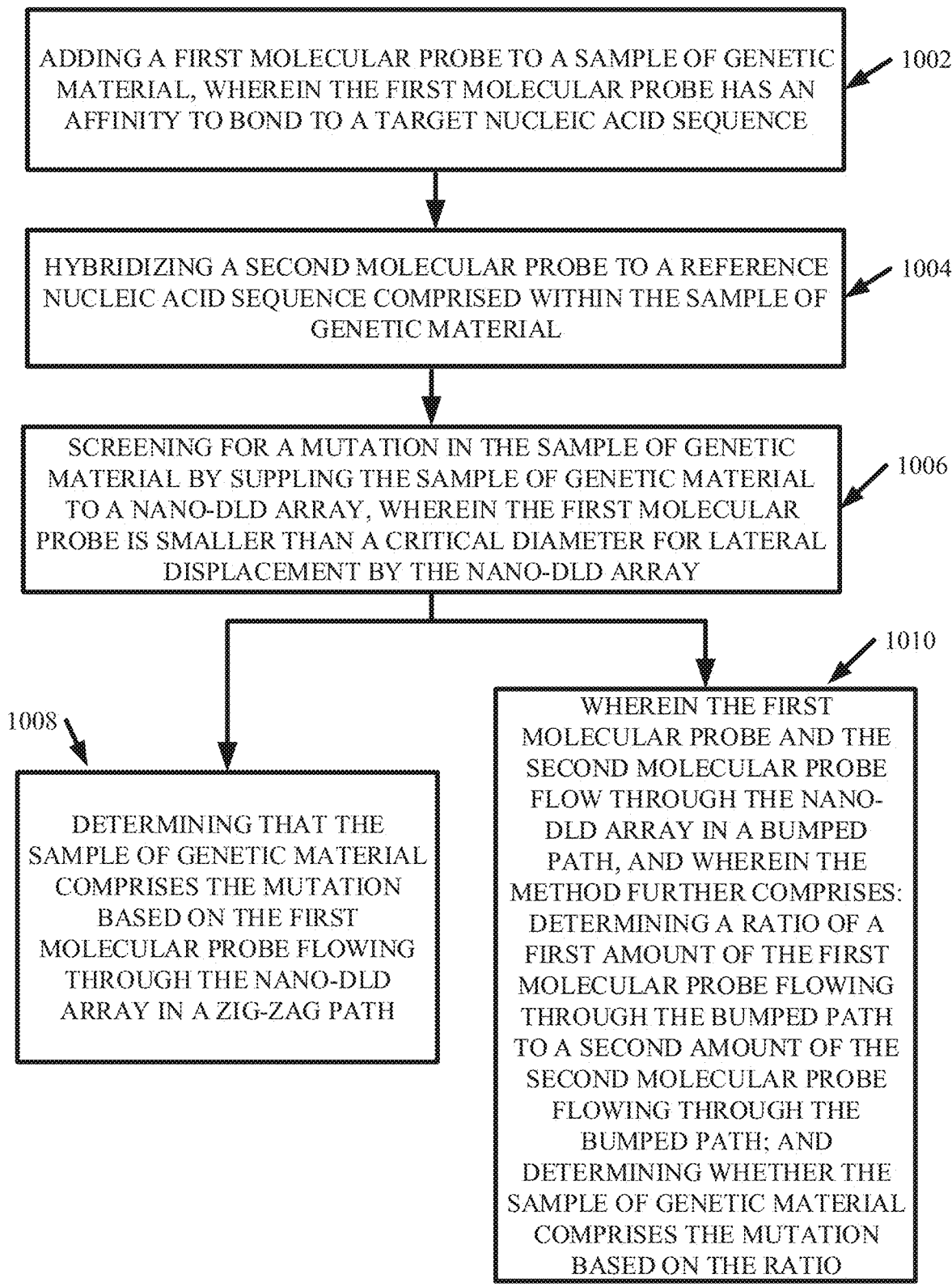

DETECTION OF MUTATIONS REGARDING ONE OR MORE DEOXYRIBONUCLEIC ACID SEQUENCES USING DETERMINISTIC LATERAL DISPLACEMENT ARRAYS

BACKGROUND

The subject disclosure relates to utilizing one or more deterministic lateral displacement arrays to detect one or more mutations regarding one or more deoxyribonucleic acid sequences, and more specifically, to utilizing one or more deterministic lateral displacement arrays, deoxyribonucleic acid hybridizations, and/or site-specific cleavage techniques to detect one or more mutations.

The amount of deoxyribonucleic acid ("DNA") that is conserved from one individual to the next is greater than 99.9%. Single nucleotide polymorphisms ("SNPs") or variants are single DNA base pairs that show variation in a minority of individuals and are the underlying source of phenotypic variability. SNPs can occur approximately once every 300 base pairs (bps) and can total approximately 10 million. Many common SNPs are documented for their association with disease and used as markers for disease detection. For example, 23 common disease-causing mutations in the cystic fibrosis transmembrane conductance regulator ("CFTR") gene associated with cystic fibrosis are routinely screened in potential carriers. However, not all disease-causing SNPs are documented or routinely screened. If a disease is present and targeted genetic testing for common mutations does not produce any results, screening for new mutations must be done.

Conventional methods use either whole-gene or whole-genome sequencing to identify novel disease-causing SNPs. One problem with said conventional methods is that they are costly and/or time-consuming, frequently requiring months or weeks. Thereby patients with the disease are left waiting for results to determine the best course of treatment, while patients who are carriers spend unnecessary healthcare dollars and/or are left anxiously waiting for results despite not having the disease. Delays due to the lengthy processing time of conventional screening methods can have a significant impact on patient treatment and/or care.

Another source of disease-causing mutations is exon copy number variant ("CNV"), which arises not from single nucleotide variations, but duplication or deletion of whole exome or regions of exosomes. However, problematically, this type of mutation is difficult to detect by conventional sequencing methods and requires an understanding of the ratio of the exon copy number to the rest of the genomic material. Similar challenges exist in detecting aberrant chromosome numbers, or aneuploidies, which typically require karyotyping. For example, problems with conventional screening techniques for CNV and/or chromosomal aneuploidy can include high costs and/or long processing times.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, apparatuses, and/or methods that can regard detecting one or more target deoxyribonucleic acid sequences via one or more deterministic lateral displacement arrays are described.

According to an embodiment, a method is provided. The method can comprise cleaving a deoxyribonucleic acid segment hybridized with a molecular probe to form a sample fluid. The cleaving can occur at a first end and a second end of the molecular probe. Also, the cleaving can comprise a cleaving agent that targets base pair mismatches. The method can also comprise supplying the sample fluid to a nanoscale deterministic lateral displacement array to screen for a single nucleotide polymorphism. An advantage of such a method can be that a low sample volume is required to perform the screening, as compare to conventional screening techniques.

In some examples, the molecular probe can remain intact between the first end and the second end subsequent to the cleaving. Also, the molecular probe can flow through the nanoscale deterministic lateral displacement array in a bumped path. An advantage of such a method can be decreased costs and/or time consumption associated with screening for SNPs, as compare to conventional techniques.

Further, in one or more examples, the cleaving can further cleave the molecular probe between the first end and the second end. Thereby, the molecular probe within the sample fluid can be too small to be laterally displaced by the nanoscale deterministic lateral displacement array. An advantage of such a method can be that site-specific cleaving can be utilized to render the screening adaptable to various nucleic acid sequences.

According to an embodiment, a method is provided. The method can comprise forming a first sample fluid by hybridizing a first molecular probe to a first deoxyribonucleic acid segment. The method can also comprise forming a second sample fluid by hybridizing a second molecular probe to a second deoxyribonucleic acid segment. The first deoxyribonucleic acid segment and the second deoxyribonucleic acid segment can be defined by a same nucleic acid sequence. Further, the method can comprise screening for a single nucleotide polymorphism in the same nucleic acid sequence by supplying the first sample fluid to a first nanoscale deterministic lateral displacement array and the second sample fluid to a second nanoscale deterministic lateral displacement array. An advantage of such a method is that a tiled panel of molecular probes can used to adjust the resolution of the screening.

In some examples, a first portion of the same nucleic acid sequence can remain intact subsequent to the cleaving of the first deoxyribonucleic acid segment. Also, a second portion of the same nucleic acid sequence can remain intact subsequent to the cleaving of the second deoxyribonucleic acid segment. Thereby, the first molecular probe can flow through the first nanoscale deterministic lateral displacement array in a first bumped path. Additionally, the second molecular probe can flow through the second nanoscale deterministic lateral displacement array in a second bumped path. Also, the molecular probe can flow through the nanoscale deterministic lateral displacement array in a bumped path. An advantage of such a method can be decreased costs and/or time consumption associated with the screen as compare to conventional techniques.

Further, in one or more examples, a portion of the same nucleic acid sequence can remain intact subsequent to the cleaving of the first deoxyribonucleic acid segment. However, the cleaving of the second deoxyribonucleic acid segment can further comprise cleaving the second deoxyribonucleic acid segment between first end and the second end of the second molecular probe. The first molecular probe can flow through the first nanoscale deterministic lateral displacement array in a bumped path. Further, the second molecular probe flows through the second nanoscale deterministic lateral displacement array in a zig-zag path. An advantage of such a method can be decreased costs and/or time consumption associated with the screen as compare to conventional techniques.

Moreover, in one or more examples, the cleaving of the first deoxyribonucleic acid segment can further comprise cleaving the first deoxyribonucleic acid segment between the first end and the second end of the first molecular probe. Also, the cleaving of the second deoxyribonucleic acid segment can further comprise cleaving the second deoxyribonucleic acid segment between first end and the second end of the second molecular probe. The first molecular probe can flow through the first nanoscale deterministic lateral displacement array in a first zig-zag path. Additionally, the second molecular probe can flow through the second nanoscale deterministic lateral displacement array in a second zig-zag path. An advantage of a such a method can be that in addition to detecting the existence of a SNP, the method can further detect a location of the SNP within the one or more deoxyribonucleic acids.

According to an embodiment, a method is provided. The method can comprise adding a first molecular probe to a sample of genetic material. The first molecular probe can have an affinity to bond to a target nucleic acid sequence. The method can also comprise hybridizing a second molecular probe to a reference nucleic acid sequence comprised within the sample of genetic material. Further, the method can comprise screening for a mutation in the sample of genetic material by supplying the sample of genetic material to a nanoscale deterministic lateral displacement array. The first molecular probe can be smaller than a critical diameter for lateral displacement by the nanoscale deterministic lateral displacement array. An advantage of such a method can be that a low sample volume is required to screen for CNVs and/or chromosomal aneuploidy, as compare to conventional screening techniques.

In some examples, the method can also comprise determining that the sample of genetic material comprises the mutation based on the first molecular probe flowing through the nanoscale deterministic lateral displacement array in a zig-zag path. An advantage of such a method can be decreased costs and/or time consumption associated with screening for CNVs and/or chromosomal aneuploidy, as compare to conventional techniques.

Further, in one or more examples, the first molecular probe and the second molecular probe can flow through the nanoscale deterministic lateral displacement array in a bumped path. Also, the method can comprise determining a ratio of a first amount of the first molecular probe flowing through the bumped path to a second amount of the second molecular probe flowing through the bumped path. Additionally, the method can comprise determining whether the sample of genetic material comprises the mutation based on the ratio. An advantage of such a method can be that the subject screening can detect various types of CNVs and/or chromosomal aneuploidy as opposed to focusing on a single type of mutation, as is commonly practiced in conventional techniques.

BRIEF DESCRIPTION OF THE DRAWINGS

FIG. 6 illustrates a flow diagram of an example, non-limiting method that can facilitate screening for SNPs using one or more deterministic lateral displacement arrays in accordance with one or more embodiments described herein.

FIG. 7 illustrates a flow diagram of an example, non-limiting method that can facilitate screening for SNPs using one or more deterministic lateral displacement arrays in accordance with one or more embodiments described herein.

FIG. 8 illustrates a flow diagram of an example, non-limiting method that can facilitate screening for SNPs using one or more deterministic lateral displacement arrays in accordance with one or more embodiments described herein.

FIG. 9 illustrates a flow diagram of an example, non-limiting method that can facilitate screening for one or more mutations in one or more DNA segments through the use of one or more deterministic lateral displacement arrays in accordance with one or more embodiments described herein.

FIG. 10 illustrates a flow diagram of an example, non-limiting method that can facilitate screening for one or more mutations in one or more DNA segments through the use of one or more deterministic lateral displacement arrays in accordance with one or more embodiments described herein.

DETAILED DESCRIPTION

Figure 1:
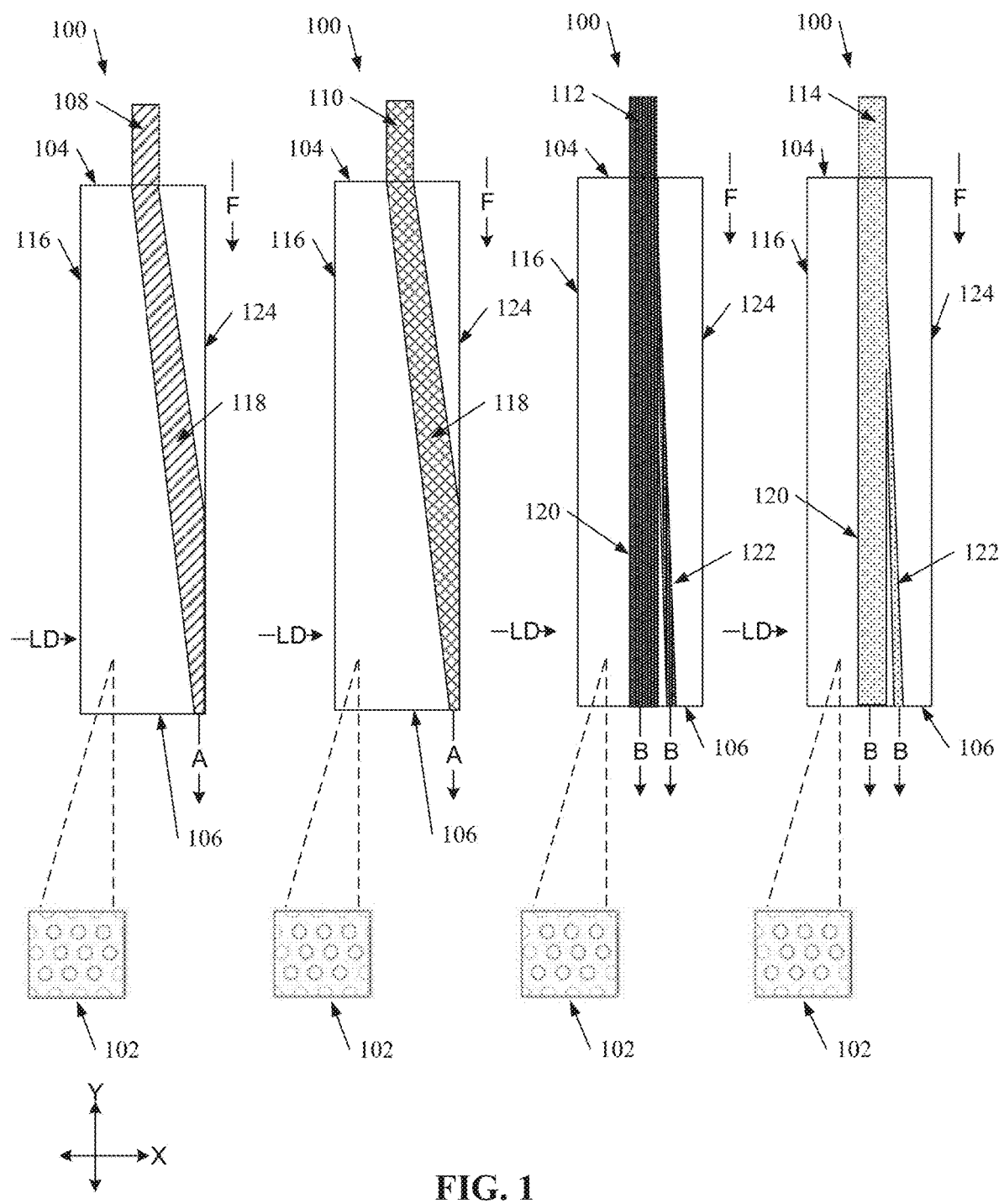
FIG. 1 illustrates a diagram of an example, non-limiting microfluidic channel that can comprise one or more deterministic lateral displacement arrays, which can facilitate screening for one or more mutations in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. Further, it is to be understood that common cross-hatching and/or shading depicted across the drawings can represent common features, compositions, and/or conditions described herein in accordance with one or more embodiments.

Given the above problems with conventional techniques for screening for mutations such as SNP, CNV, and/or chromosomal aneuploidy; the present disclosure can be implemented to produce a solution to one or more of these problems in the form of screening DNA segments for mutations using deterministic lateral displacement arrays. Methods and/or systems implementing such screening can have the advantage of being less costly and/or less time-consuming than conventional screening techniques. Additionally, other advantages exhibited by the methods and/or systems described herein, as compared to conventional techniques, can include, but are not limited to: rapid detection, the capability of single-particle detection, lower sample volumes required for detection and/or preparation, a direct read-out of screening results, and/or unprecedented adaptability to numerous DNA sequences.

Various embodiments described herein can regard rapid single molecule detection that can screen for mutations substantially faster and/or cheaper than conventional techniques. Further, one or more embodiments can utilize microfluidics in a lab-on-a-chip device to screen one or more DNA segments via deterministic lateral displacement (e.g., via one or more nanoscale deterministic lateral displacement arrays). For example, one or more embodiments can detect SNPs, CNV, and/or chromosomal aneuploidy. Thus, one or more embodiments described herein can regard one or more lab-on-chip devices that can facilitate screening for one or more mutations, wherein the one or more lab-on-chip devices can, advantageously, be operated quickly (e.g., near instantaneously), in a variety of locations (e.g., at an entity's home), and without the typical need for specialized laboratory equipment.

As used herein, the term "lab-on-a-chip ("LOC")" can refer to one or more devices that can integrate one or more laboratory functions onto an integrated circuit (e.g., a semiconductor substrate structure) to achieve autonomous screening of one or more samples. LOCs can utilize microelectromechanical systems and/or microfluidic systems to facilitate screening the one or more samples. One of ordinary skill in the art will recognize that a LOC devices can range in size from, for example, one or more square millimeters to one or more square centimeters.

As used herein the term "deterministic lateral displacement ("DLD")" can refer to one or more microfluidic techniques that can size fractionate a polydisperse suspension of molecules through the use of one or more arrays of obstacles. For example, DLD arrays can laterally displace target molecules within a sample stream based on size. Further, DLD arrays can comprise a plurality of pillars arranged in a lattice structure. Rows of pillars comprising the lattice structure can be positioned offset of each other at a defined angle, and pillars can be separated from each other by a defined gap size. The defined angle and/or gap size can facilitate displacement of one or more molecules of a target size range comprised within a stream flowing through the DLD array.

As used herein the term "nano-DLD array" can refer to a DLD array that can be characterized by one or more dimensions ranging from greater than or equal to 1 nanometer (nm) and less than or equal to 999 nm. For example, a nano-DLD array can be a DLD array characterized by a gap size (e.g., a distance between adjacent pillars comprised within the lattice structure) of greater than or equal to 1 nm and less than or equal to 999 nm (e.g., greater than or equal to 25 nm and less than or equal to 235 nm). In one or more embodiments, a nano-DLD array can facilitate displacement of genetic code sequences that can be characterized as having an exemplary length ranging from, but not limited to, greater than or equal to 25 bp and less than or equal to 200 bp.

As used herein the term "mutation" can refer to a change in a genetic sequence (e.g., naturally occurring or synthesized). For example, a mutation can comprise the changing of the structure of a gene and/or genetic material, resulting in a variant form that can be transmitted to subsequent generations of the gene and/or genetic material. A mutation can be caused by the alteration of one or more base pairs in a DNA segment, and/or the deletion, insertion, and/or rearrangement of one or more sections of genes and/or chromosomes. Example mutations can include, SNPs, CNVs, chromosomal aneuploidy, exon deletion and/or amplification, a combination thereof, and/or the like.

FIG. 1 illustrates a diagram of example, non-limiting microfluidic channels 100 that can comprise one or more nano-DLD arrays 102, which can facilitate screening for one or more SNPs through lateral displacement of one or more molecules based on size in accordance with one or more embodiments described herein. The one or more microfluidic channels 100 can comprise one or more inlets 104 and/or one or more outlets 106. One or more sample fluids (e.g., first sample fluid 108, second sample fluid 110, third sample fluid 112, and/or fourth sample fluid 114) can enter the one or more microfluidic channels 100 via the one or more inlets 104 and flow through the one or more nano-DLD arrays 102 (e.g., in a flow direction represented by the "F" arrow in FIG. 1) to exit the one or more microfluidic channels 100 via the one or more outlets 106. FIG. 1 depicts a focused injection configuration of the one or more microfluidic channels 100 in which the one or more sample fluids (e.g., first sample fluid 108, second sample fluid 110, third sample fluid 112, and/or fourth sample fluid 114) can enter the one or more microfluidic channels 100 in a focused region of the microfluidic channels' 100 width (e.g., along the "X" direction). While FIG. 1 depicts the focused region within the center of the microfluidic channel's 100 width, the architecture of the one or more microfluidic channels 100 is not so limited. For example, the focused region can be closer to the one or more side walls 116 than depicted in FIG. 1.

In another example, the one or more microfluidic channels 100 can comprise a full-width injection configuration in which the one or more sample fluids (e.g., first sample fluid 108, second sample fluid 110, third sample fluid 112, and/or fourth sample fluid 114) can enter the one or more microfluidic channels 100 across the entire, and/or nearly the entire, width (e.g., along the "X" direction) of the one or more microfluidic channels 100.

The one or more nano-DLD arrays 102 can comprise a lattice of asymmetric pillars arranged in rows and/or columns. FIG. 1 shows an expanded view (e.g., as indicated by dashed lines) of a portion of the one or more nano-DLD arrays 102 to illustrate an exemplary structure. As shown in the expanded portion, the plurality of pillars comprised within the one or more nano-DLD arrays 102 can be arranged at an angle with respect to one or more side walls 116 of the one or more microfluidic channels 100, such that one or more rows and/or columns of the pillars can be offset from adjacent rows and/or columns of the pillars. For example, the angle can be greater than or equal to 0 degrees and less than or equal to 90 degrees. The one or more nano-DLD arrays 102 can extend across a portion and/or an entirety of the width (e.g., along the "X" direction) of the one or more microfluidic channels 100. Also, the one or more nano-DLD arrays 102 can extend across a portion and/or an entirety of the length (e.g., along the "Y" direction) of the one or more microfluidic channels 100. Further, the one or more nano-DLD arrays 102 can have a uniform gap size between pillars along the width (e.g., along the "X" direction) and/or length (e.g., along the "Y" direction) of the one or more microfluidic channels 100. Alternatively, the one or more nano-DLD arrays 102 can have varying gap sizes between pillars along the width (e.g., along the "X" direction) and/or length (e.g., along the "Y" direction) of the one or more microfluidic channels 100. For example, the gap size of the one or more nano-DLD arrays 102 can decrease (e.g., gradually and/or abruptly) along the length (e.g., along the "Y" direction) of the one or more microfluidic channels 100.

Figure 2A:
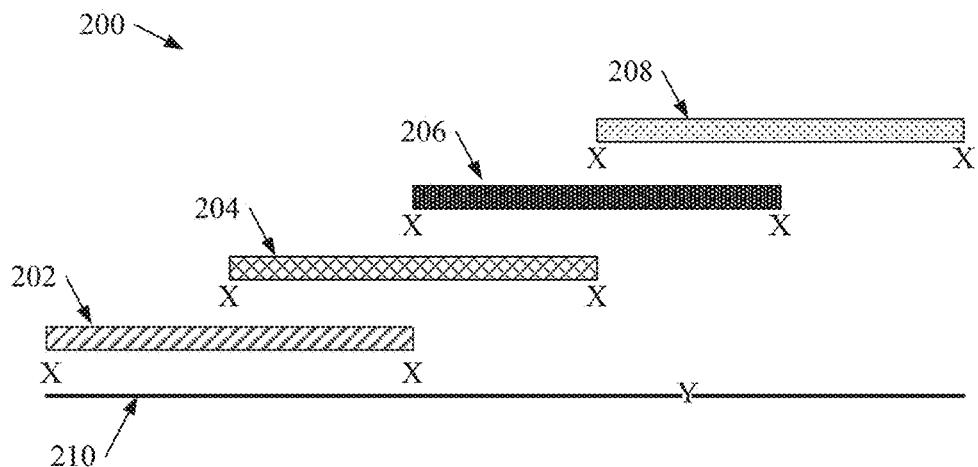
FIG. 2A illustrates a diagram of an example, non-limiting hybridization scheme than depict how one or more respective molecular probes can have an affinity to bond to respective portions of one or more genetic materials in accordance with one or more embodiments described herein.

FIG. 2A illustrates a diagram of an exemplary, non-limiting hybridization scheme 200 that can depict how respective molecular probes (e.g., first molecular probe 202, second molecular probe 204, third molecular probe 206, and/or fourth molecular probe 208) can have different binding affinities and/or can be hybridized to different portions of one or more genetic materials 210 to facilitate preparation of the one or more sample fluids (e.g., first sample fluid 108, second sample fluid 110, third sample fluid 112, and/or fourth sample fluid 114) in accordance with one or more embodiments described herein. Repetitive description of like elements employed in other embodiments described herein is omitted for sake of brevity.

The one or more sample fluids (e.g., first sample fluid 108, second sample fluid 110, third sample fluid 112, and/or fourth sample fluid 114) can comprise one or more genetic materials 210. Example samples from which the one or more genetic materials 210 can be derived from can include, but are not limited to: in vitro samples, blood samples, urine samples, tissue samples, saliva samples, a combination thereof, and/or the like. For example, the one or more genetic materials 210 can comprise, but are not limited to: DNA from clinical samples, isolated genomic DNA, purified DNA, chromosomes, genes, a combination thereof, and/or the like.

In one or more embodiments, multiple sample fluids (e.g., first sample fluid 108, second sample fluid 110, third sample fluid 112, and/or fourth sample fluid 114) can be prepared by hybridizing the one or more genetic materials 210 (e.g., one or more DNA segments) with respective molecular probes (e.g., first molecular probe 202, second molecular probe 204, third molecular probe 206, and/or fourth molecular probe 208). For example, each respective molecular probe (e.g., first molecular probe 202, second molecular probe 204, third molecular probe 206, and/or fourth molecular probe 208) can have an affinity to bond to a different nucleic acid sequence defining a portion of the genetic material 210.

As shown in FIG. 2A, respective molecular probes (e.g., first molecular probe 202, second molecular probe 204, third molecular probe 206, and/or fourth molecular probe 208) can be hybridized to respective portions of the one or more genetic materials 210 (e.g., DNA segments). For example, the first sample fluid 108 can be prepared by hybridizing the one or more genetic materials 210 with the first molecular probe 202. In another example, the second sample fluid 110 can be prepared by hybridizing the one or more genetic materials 210 with the second molecular probe 204. In another example, the third sample fluid 112 can be prepared by hybridizing the one or more genetic materials 210 with the third molecular probe 206. In another example, the fourth sample fluid 114 can be prepared by hybridizing the one or more genetic materials 210 with the fourth molecular probe 208.

Also, as shown in FIG. 2A, the straight horizontal line of the genetic material 210 can represent a nucleic acid sequence that can define the genetic material 210 (e.g., a nucleic acid sequence that can define a DNA segment). In one or more embodiments, one or more molecular probes (e.g., first molecular probe 202, second molecular probe 204, third molecular probe 206, and/or fourth molecular probe 208) can hybridize to a first portion of the genetic material 210 while one or more other molecular probes (e.g., first molecular probe 202, second molecular probe 204, third molecular probe 206, and/or fourth molecular probe 208) can hybridize to one or more other portions of the genetic material 210. In one or more embodiments, the first portion can be entirely separate (e.g., adjacent) from the one or more other portions. Alternatively, in one or more embodiments one or more of the other portions can overlap the first portion, as shown in FIG. 2A; thereby the one or more molecular probes (e.g., first molecular probe 202, second molecular probe 204, third molecular probe 206, and/or fourth molecular probe 208) can comprise a tiled panel of molecular probes. Further, the tiling density of the tiled panel of molecular probes can vary. For example, greater than or equal to 50 percent (%) and less than or equal to 100% of one or more of the other portions can overlap the first portion.

While FIG. 2A illustrates a hybridization scheme 200 comprising four respective molecular probes (e.g., first molecular probe 202, second molecular probe 204, third molecular probe 206, and/or fourth molecular probe 208) to facilitate the preparation of four respective sample fluids (e.g., first sample fluid 108, second sample fluid 110, third sample fluid 112, and/or fourth sample fluid 114), the architecture of the hybridization scheme 200 is not so limited. For example, the hybridization scheme 200 can comprise fewer or additional respective molecular probes to facilitate the preparation of fewer or additional sample fluids. One of ordinary skill in the art will recognize that the number of respective molecular probes, and thereby the number of respective sample fluids, can vary depending on the size of the genetic material 210 and/or the intended purpose of the screening.

The one or more molecular probes (e.g., first molecular probe 202, second molecular probe 204, third molecular probe 206, and/or fourth molecular probe 208) can be characterized as molecules that have an affinity to bond (e.g., covalently bod) to a defined nucleic acid sequence. For example, the one or more molecular probes (e.g., first molecular probe 202, second molecular probe 204, third molecular probe 206, and/or fourth molecular probe 208) can comprise one or more nucleic acid sequences that are complimentary to one or more nucleic acid sequences defining the genetic material 210 (e.g., DNA segments).

Furthermore, the molecular probes (e.g., first molecular probe 202, second molecular probe 204, third molecular probe 206, and/or fourth molecular probe 208) can be larger than the one or more critical diameters of the one or more nano-DLD arrays 102 comprised within the one or more microfluidic channels 100. As used herein, the term "critical diameter" can refer to a defined threshold that can characterize a size at which molecules are subject to displacement (e.g., lateral displacement) by a subject nano-DLD array 102. In other words, molecules having a size greater than or equal to the critical diameter of a subject nano-DLD array 102 can be displaced towards a collection region by the nano-DLD array 102. The critical diameter of one or more nano-DLD arrays 102 can be affected by one or more parameters of the nano-DLD arrays 102, such as gap size and/or the offset angle (e.g., represented by "θ").

For example, a size of the one or more molecular probes (e.g., first molecular probe 202, second molecular probe 204, third molecular probe 206, and/or fourth molecular probe 208) can range from, but is not limited to, greater than or equal to 25 bp and less than or equal 20,000 bp. One or more users of the one or more microfluidic channels 100 can select molecular probe sizes based on, for example, the critical diameter of the one or more nano-DLD arrays 102 and/or the size of the genetic material 210. Additionally, the one or more molecular probes (e.g., first molecular probe 202, second molecular probe 204, third molecular probe 206, and/or fourth molecular probe 208) can be labelled to facilitate detection of the one or more molecular probes as they enter, traverse, and/or exit the one or more microfluidic channels 100. For example, the one or more molecular probes (e.g., first molecular probe 202, second molecular probe 204, third molecular probe 206, and/or fourth molecular probe 208) can exit the one or more outlets 106 at one or more locations depending on the one or more molecular probes' interaction with the one or more nano-DLD arrays 102 (e.g., whether the one or more molecular probes are bumped towards a collection region or zig-zag through the one or more nano-DLD arrays 102). In one or more embodiments, respective molecular probes (e.g., first molecular probe 202, second molecular probe 204, third molecular probe 206, and/or fourth molecular probe 208) can be labelled with respective identifiers.

In one or more embodiments, the one or more molecular probes (e.g., first molecular probe 202, second molecular probe 204, third molecular probe 206, and/or fourth molecular probe 208) can be labeled with one or more fluorescent tags (e.g., natural and/or synthetic fluorescent tags) to render the one or more molecular probes fluorescent and/or more readily identified by optical detection techniques. The one or more fluorescent tags can be, for example, bonded to the respective molecular backbones of the one or more molecular probes (e.g., first molecular probe 202, second molecular probe 204, third molecular probe 206, and/or fourth molecular probe 208). Example fluorescent labeling techniques that can facilitate detection of the one or more molecular probes can include, but are not limited to: enzymatic labeling, chemical labeling, protein labeling, genetic labeling, DNA intercalating agents, a combination thereof, and/or the like. One of ordinary skill in the art will recognize that a variety of known fluorescent labelling techniques can be utilized to label the one or more molecular probes (e.g., first molecular probe 202, second molecular probe 204, third molecular probe 206, and/or fourth molecular probe 208) for detection by one or more sensor devices.

Further, in various embodiments, the one or more molecular probes (e.g., first molecular probe 202, second molecular probe 204, third molecular probe 206, and/or fourth molecular probe 208) can be labelled using one or more magnetic beads to render the one or more molecular probes more readily identified by electrical detection techniques. Example magnetic bead surface chemistries can include, but are not limited to: silica, oligo, specific oligonucleotide sequences, and/or the like. The one or more magnetic beads can be bonded to the one or more molecular probes (e.g., first molecular probe 202, second molecular probe 204, third molecular probe 206, and/or fourth molecular probe 208) to facilitate detecting the one or more molecular probes through triggered electrical shifts. One of ordinary skill in the art will recognize that a variety of known magnetic and/or electrochemical techniques can be used to render the one or more molecular probes (e.g., first molecular probe 202, second molecular probe 204, third molecular probe 206, and/or fourth molecular probe 208) readily identifiable by one or more sensor devices.

In one or more embodiments, the one or more sample fluids (e.g., first sample fluid 108, second sample fluid 110, third sample fluid 112, and/or fourth sample fluid 114) can be prepared by one or more hybridization reactions between the one or more molecular probes (e.g., first molecular probe 202, second molecular probe 204, third molecular probe 206, and/or fourth molecular probe 208) and/or the one or more genetic materials 210 (e.g., DNA segments). The one or more hybridization reactions can be facilitated using enzymatic hybridization techniques and/or temperature based hybridization techniques. For example, the one or more sample fluids (e.g., first sample fluid 108, second sample fluid 110, third sample fluid 112, and/or fourth sample fluid 114) can be annealed to a temperature ranging from, but not limited to, greater than or equal to 50 degrees Celsius ("° C.") and less than or equal to 100° C. (e.g., 95° C.).

Further, preparation of the one or more sample fluids (e.g., first sample fluid 108, second sample fluid 110, third sample fluid 112, and/or fourth sample fluid 114) can comprise site-specific cleaving of the genetic material 210. The cleaving can comprise chemical cleaving techniques and/or enzymatic cleaving techniques. For example, the cleaving can comprise the use of a chemical cleaving agent such as piperidine and/or hydroxlamine. In another example, the cleaving can comprise the use of an enzymatic cleaving agent such as endonucleases. In one or more embodiments, the cleaving agent can target base pair mismatches between a respective molecular probe (e.g., first molecular probe 202, second molecular probe 204, third molecular probe 206, and/or fourth molecular probe 208) and the genetic material 210 comprising a respective sample fluid (e.g., first sample fluid 108, second sample fluid 110, third sample fluid 112, and/or fourth sample fluid 114).

Thus, the site-specific cleaving can be facilitated by engineered mismatches (e.g., represented by exemplary "X"s in FIGS. 2A and/or 2B) and/or non-engineered mismatches caused by mutations in the nucleic acid sequence that defines the one or more genetic materials 210 (e.g., represented by an exemplary "Y"s in FIGS. 2A and/or 2B). For example, respective ends (e.g., the 5' end and/or the 3' end) of the respective molecular probes (e.g., first molecular probe 202, second molecular probe 204, third molecular probe 206, and/or fourth molecular probe 208) can mismatch the corresponding base pairs in the genetic material 210. For instance, the respective molecular probes (e.g., first molecular probe 202, second molecular probe 204, third molecular probe 206, and/or fourth molecular probe 208) can have an engineered mismatch (e.g., represented by "X" in FIGS. 2A and/or 2B) at a first end (e.g., their 5' end) and/or a second end (e.g., their 3' end) in comparison to reference nucleic acid sequence, which can represent a standard and/or healthy nucleic acid sequence to be hybridized by the respective molecular probe (e.g., first molecular probe 202, second molecular probe 204, third molecular probe 206, and/or fourth molecular probe 208).

In another example, a variation in the nucleic acid sequence defining the genetic material 210 as compared to a reference nucleic acid sequence, which can represent a nucleic acid sequence that can define a standard and/or healthy variant of the genetic material 210 (e.g., DNA segment), can cause one or more non-engineered mismatches (e.g., represented by "Y" in FIGS. 2A and/or 2B). The one or more non-engineered mismatches (e.g., represented by "Y" in FIGS. 2A and/or 2B) can be an indication of a mutation in the genetic material 210, such as one or more SNPs.

Figure 2B:
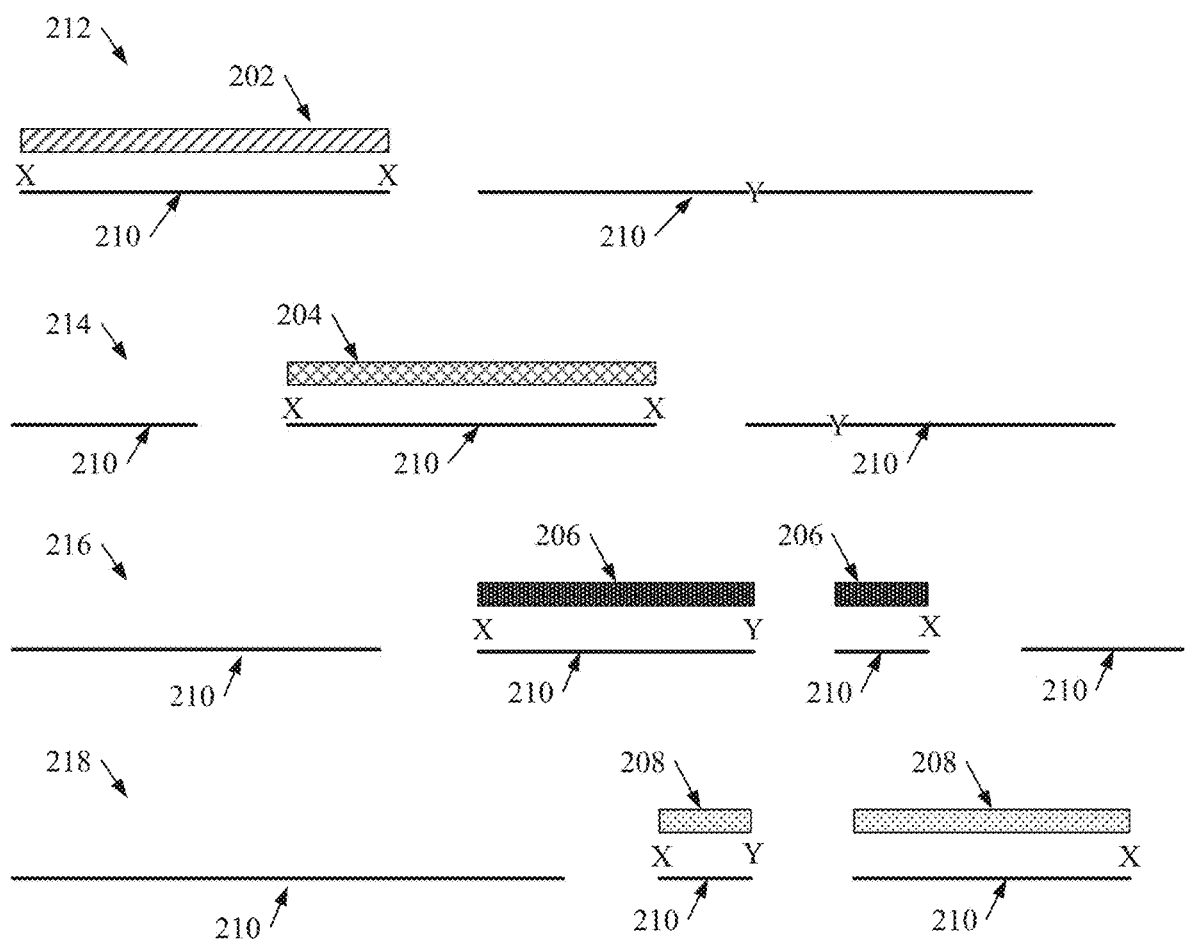
FIG. 2B illustrates a diagram of example, non-limiting cleaving schemes that can depict how one or more respective molecular probes can be cleaved to facilitate screening for one or more mutations in accordance with one or more embodiments described herein.

FIG. 2B illustrates a diagram of example, non-limiting cleaving schemes that can depict how the genetic material 210 can be cleaved in preparation of the one or more sample fluids (e.g., first sample fluid 108, second sample fluid 110, third sample fluid 112, and/or fourth sample fluid 114) to facilitate screening for one or more mutations, such as SNPs, via one or more deterministic lateral displacement arrays 102 in accordance with one or more embodiments described herein. Repetitive description of like elements employed in other embodiments described herein is omitted for sake of brevity.

The first cleaving scheme 212 can depict cleaving of the genetic material 210 (e.g., DNA segment) in accordance with the exemplary hybridization scheme 200 to prepare the first sample fluid 108. As shown in FIG. 2A, the first molecular probe 202 can hybridize to a portion of the genetic material 210 that does not comprise a non-engineered mismatch (e.g., represented by "Y" in FIGS. 2A and/or 2B), such as a SNP. As shown in FIG. 2B, the chemical and/or enzymatic cleaving (e.g., via one or more cleaving agents that target mismatched base pairs) of the genetic material 210 hybridized by the first molecular probe 202 can result in cleaving of the genetic material 210 at the 5' end and/or the 3' end of the first molecular probe 202. Since, no non-engineered mismatches are comprised within the portion of the genetic material 210 hybridized between the 5' end and the 3' end of the first molecular probe 202, the nucleic acid sequence defining the first molecular probe 202 remains consistent (e.g., intact) before and after the site-specific cleaving. Thus, the genetic material 210 can be comprised within the first sample fluid 108 as two segments (e.g., a first segment hybridized with the first molecular probe 202, and a second segment not hybridized with the first molecular probe 202).

The second cleaving scheme 214 can depict cleaving of the genetic material 210 (e.g., DNA segment) in accordance with the exemplary hybridization scheme 200 to prepare the second sample fluid 110. As shown in FIG. 2A, the second molecular probe 204 can hybridize to a portion of the genetic material 210 that does not comprise a non-engineered mismatch (e.g., represented by "Y" in FIGS. 2A and/or 2B), such as a SNP. As shown in FIG. 2B, the chemical and/or enzymatic cleaving (e.g., via one or more cleaving agents that target mismatched base pairs) of the genetic material 210 hybridized by the second molecular probe 204 can result in cleaving of the genetic material 210 at the 5' end and/or the 3' end of the second molecular probe 204. Since, no non-engineered mismatches are comprised within the portion of the genetic material 210 hybridized between the 5' end and the 3' end of the second molecular probe 204, the nucleic acid sequence defining the second molecular probe 204 remains consistent (e.g., intact) before and after the site-specific cleaving. Thus, the genetic material 210 can be comprised within the second sample fluid 110 as three segments (e.g., one segment hybridized with the second molecular probe 204, and two other segments not hybridized with the second molecular probe 204).

The third cleaving scheme 216 can depict cleaving of the genetic material 210 (e.g., DNA segment) in accordance with the exemplary hybridization scheme 200 to prepare the third sample fluid 112. As shown in FIG. 2A, the third molecular probe 206 can hybridize to a portion of the genetic material 210 that comprises a non-engineered mismatch (e.g., represented by "Y" in FIGS. 2A and/or 2B), such as a SNP. As shown in FIG. 2B, the chemical and/or enzymatic cleaving (e.g., via one or more cleaving agents that target mismatched base pairs) of the genetic material 210 hybridized by the third molecular probe 206 can result in cleaving of the genetic material 210 at the 5' end of the third molecular probe 206, the 3' end of the third molecular probe 206, and/or at the non-engineered mismatch (e.g., represented by "Y" in FIGS. 2A and/or 2B). Since, a non-engineered mismatch (e.g., represented by "Y" in FIGS. 2A and/or 2B) is comprised within the portion of the genetic material 210 hybridized between the 5' end and the 3' end of the third molecular probe 206, the nucleic acid sequence defining the third molecular probe 206 can be cleaved between the 5' end of the third molecular probe 206 and the 3' end of the third molecular probe 206. Thus, the genetic material 210 can be comprised within the third sample fluid 112 as four segments (e.g., a first segment hybridized with a first segment of the third molecular probe 206, a second segment hybridized with a second segment of the third molecular probe 206, and/or two additional segments not hybridized with the third molecular probe 206).

The fourth cleaving scheme 218 can depict cleaving of the genetic material 210 (e.g., DNA segment) in accordance with the exemplary hybridization scheme 200 to prepare the fourth sample fluid 114. As shown in FIG. 2A, the fourth molecular probe 208 can hybridize to a portion of the genetic material 210 that comprises a non-engineered mismatch (e.g., represented by "Y" in FIGS. 2A and/or 2B), such as a SNP. As shown in FIG. 2B, the chemical and/or enzymatic cleaving (e.g., via one or more cleaving agents that target mismatched base pairs) of the genetic material 210 hybridized by the fourth molecular probe 208 can result in cleaving of the genetic material 210 at the 5' end of the fourth molecular probe 208, the 3' end of the fourth molecular probe 208, and/or at the non-engineered mismatch (e.g., represented by "Y" in FIGS. 2A and/or 2B). Since, a non-engineered mismatch (e.g., represented by "Y" in FIGS. 2A and/or 2B) is comprised within the portion of the genetic material 210 hybridized between the 5' end and the 3' end of the fourth molecular probe 208, the nucleic acid sequence defining the fourth molecular probe 208 can be cleaved between the 5' end of the third molecular probe 206 and the 3' end of the third molecular probe 206. Thus, the genetic material 210 can be comprised within the fourth sample fluid 115 as three segments (e.g., a first segment hybridized with a first segment of the fourth molecular probe 208, a second segment hybridized with a second segment of the fourth molecular probe 208, and/or a third segment not hybridized with the fourth molecular probe 208).

Moreover, in one or more embodiments, the one or more sample fluids (e.g., first sample fluid 108, second sample fluid 110, third sample fluid 112, and/or fourth sample fluid 114) can be prepared off a LOC comprising the one or more microfluidic channels 100 and/or can be loaded onto the LOC, and/or can thereby enter the one or more microfluidic channels 100 subsequent to preparation. Also, in various embodiments the one or more sample fluids (e.g., first sample fluid 108, second sample fluid 110, third sample fluid 112, and/or fourth sample fluid 114) can be prepared on a LOC comprising the one or more microfluidic channels 100.

Referring again to FIG. 1, screening of the one or more sample fluids (e.g., first sample fluid 108, second sample fluid 110, third sample fluid 112, and/or fourth sample fluid 114) for one or more mutations (e.g., SNPs) can be facilitated by the one or more microfluidic channels 100. For example, one or more LOCs can comprise a respective microfluidic channel 100 for each sample fluid (e.g., first sample fluid 108, second sample fluid 110, third sample fluid 112, and/or fourth sample fluid 114). Just as the number of molecular probes is not limited to the exemplary four molecular probes described with regards to FIGS. 1-2B, the number of sample fluids and/or microfluidic channels 100 is not limited to four. For example, one of ordinary skill in the art will recognize that the number of sample fluids and/or microfluidic channels 100 can be fewer or greater than the four illustrated herein depending on, for instance: the desired resolution of the scanning, the size of the subject genetic material 210, and/or the desired specificity with regards to one or more detected SNPs.

As the respective sample fluids (e.g., first sample fluid 108, second sample fluid 110, third sample fluid 112, and/or fourth sample fluid 114) flow through the one or more nano-DLD arrays 102 (e.g., in the flow direction represented by arrow "F"), respective molecular probes (e.g., first molecular probe 202, second molecular probe 204, third molecular probe 206, and/or fourth molecular probe 208) can experience different flow paths based on the size of the molecules. In other words, the one or more nano-DLD arrays 102 can displace respective molecular probes (e.g., first molecular probe 202, second molecular probe 204, third molecular probe 206, and/or fourth molecular probe 208) based on size.

The respective molecular probes (e.g., first molecular probe 202, second molecular probe 204, third molecular probe 206, and/or fourth molecular probe 208) can be larger than the critical diameter of the one or more nano-DLD arrays 102. Thus, respective molecular probes (e.g., first molecular probe 202 and/or second molecular probe 204) can flow through the one or more nano-DLD arrays 102 in a bumped path 118 when they remain un-cleaved between their 5' end and/or 3' end by the site-specific cleaving. In contrast, respective molecular probes cleaved between the molecular probes 5' end and/or 3' end by the site-specific cleaving (e.g., third molecular probe 206 and/or fourth molecular probe 208) can be smaller than the critical diameter of the one or more nano-DLD arrays 102, and thereby can flow through the one or more nano-DLD arrays 102 in a zig-zag path 120 and/or partially bumped path 122.

The bumped path 118 can comprise a flow path through the one or more nano-DLD arrays 102 wherein the respective molecular probe (e.g., first molecular probe 202 and/or second molecular probe 204) can be laterally displaced (e.g., in a lateral displacement direction represented by the "LD" arrow) towards a collection region (e.g., a collection wall 124 and/or a collection channel). For example, the one or more intact molecular probes (e.g., molecular probes not cleaved between the molecular probe's 5' end and/or 3' end) can be laterally displaced towards a collection wall 124 of the one or more microfluidic channels 100. As the one or more intact molecular probes (e.g., first molecular probe 202 and/or second molecular probe 204) flow through the one or more nano-DLD arrays 102, the one or more intact molecular probes (e.g., first molecular probe 202 and/or second molecular probe 204) can be further displaced towards and/or concentrated adjacent to the collection wall 124. Thus, the one or more intact molecular probes (e.g., first molecular probe 202 and/or second molecular probe 204) can exit the one or more microfluidic channels 100 via the one or more outlets 106 as a concentrated stream (e.g., as represented by arrow "A"). Therefore, the one or more intact molecular probes (e.g., first molecular probe 202 and/or second molecular probe 204), being larger than the critical diameter of the one or more nano-DLD arrays 102, can flow through the one or more nano-DLD arrays 102 in a bumped path 118.

The zig-zag path 120 can comprise a flow path through the one or more nano-DLD arrays 102 wherein the respective molecular probe (e.g., third molecular probe 206 and/or fourth molecular probe 208) can zig-zag around the plurality of pillars within the nano-DLD array 102, thereby avoiding persistent lateral displacement towards the collection region (e.g., collection wall 124). For example, the one or more cleaved molecular probes (e.g., third molecular probe 206 and/or fourth molecular probe 208) can be smaller than the critical diameter of the one or more nano-DLD arrays 102 (e.g., due at least to the site-specific cleaving) and can thereby flow through the one or more nano-DLD arrays 102 in a zig-zag path 120 and/or exit the one or more nano-DLD arrays 102 in another stream (e.g., as represented by arrow "B"). Additionally, one or more of the cleaved molecular probes (e.g., third molecular probe 206 and/or fourth molecular probe 208) can be partially displaced, wherein the one or more cleaved molecular probes can flow through the one or more nano-DLD arrays 102 in a partial bumped path 122. The one or more molecular probes can be partially bumped (e.g., partially laterally displaced) at least because their size and/or length is close to the critical diameter.

Thus, in one or more embodiments, whether or not a given portion of a genetic material 210 (e.g., DNA segment) comprises one or more SNPs can be determined based on the flow path (e.g., bumped path 118 or zig-zag path 120) of the respective molecular probe (e.g., first molecular probe 202, second molecular probe 204, third molecular probe 206, and/or fourth molecular probe 208) having an affinity to bond to said portion (e.g., said nucleic acid sequence) of the genetic material 210. If a portion of the genetic material 210 (e.g., DNA segment) contains no SNPs; then the site-specific cleaving can cleave said portion only at the engineered mismatches located at the 5' end and/or 3' end of a molecular probe having an affinity to bond to said portion, said molecular probe can remain un-cleaved between its 5' end and 3' end (e.g., the nucleic acid sequence defining the molecular probe can remain intact throughout preparation of the respective sample fluid), and/or said molecular probe can flow through the one or more nano-DLD arrays 102 in a bumped path 118. If a portion of the genetic material 210 (e.g., DNA segment) comprises one or more SNPs; then the site-specific cleaving can cleave said portion at the engineered mismatches located at the 5' end and/or 3' end of a molecular probe having an affinity to bond to said portion and at the non-engineered mismatches located at the SNP, said molecular probe can be cleaved between the its 5' end and 3' end (e.g., at a point corresponding to the SNP), and/or said molecular probe can flow through the one or more nano-DLD arrays 102 in a zig-zag path 120 and/or partially bumped path 122.

In one or more embodiments, the use of a plurality of molecular probes (e.g., first molecular probe 202, second molecular probe 204, third molecular probe 206, and/or fourth molecular probe 208), which can have respective binding affinities towards distinct portions of the genetic material 210 (e.g., DNA segment), can facilitate a user of the one or more microfluidic channels 100 in identifying the one or more specific portions of the genetic material 210 that comprise one or more SNPs. For instance, with regards to the exemplary hybridization scheme 200 and/or genetic material 210 shown in FIG. 2A, the use of four molecular probes (e.g., first molecular probe 202, second molecular probe 204, third molecular probe 206, and/or fourth molecular probe 208), which can have respective binding affinities towards distinct portions ranging across the entirety of the genetic material 210, can facilitate a user in identifying that the specific portions hybridized with the third molecular probe 206 and/or the fourth molecular probe 208 can comprise one or more SNPs (e.g., as indicated by the zig-zag paths 120 shown in FIG. 1).

Furthermore, in one or more embodiments, the use of a tiled panel of molecular probes (e.g., first molecular probe 202, second molecular probe 204, third molecular probe 206, and/or fourth molecular probe 208), as shown in FIG. 2A, can further narrow the potential location the one or more SNPs. For instance, with regards to the exemplary hybridization scheme 200 and/or genetic material 210 shown in FIG. 2A, since the third molecular probe 206 and the fourth molecular probe 208 both exhibited zig-zag paths 120, the portion of genetic material 210 comprising the one or more SNPs can be narrowed to a portion overlapped by the bonding affinities of the third molecular probe 206 and/or the fourth molecular probe 208. Thus, the one or more embodiments described herein can advantageously determine whether a genetic material 210 comprises one or more SNPs and/or identify the possible location of the one or more SNPs.

Additionally, in various embodiments, once a portion of the genetic material 210 comprising one or more SNPs has been identified (e.g., via the flow path of the third molecular probe 206 and/or the fourth molecular probe 208), the location of the SNP within said portion can further be narrowed by preparing new sample fluids using higher tile density with regards to said identified portion of the genetic material 210. In other words, the various features of the one or more embodiments described herein can be repeated with increases specificity (e.g., with regards to the one or more molecular probes and/or the parameters, such as gap size, of the one or more nano-DLD arrays 102) until the exact base pair that is mutated can be identified.

Figure 3A:
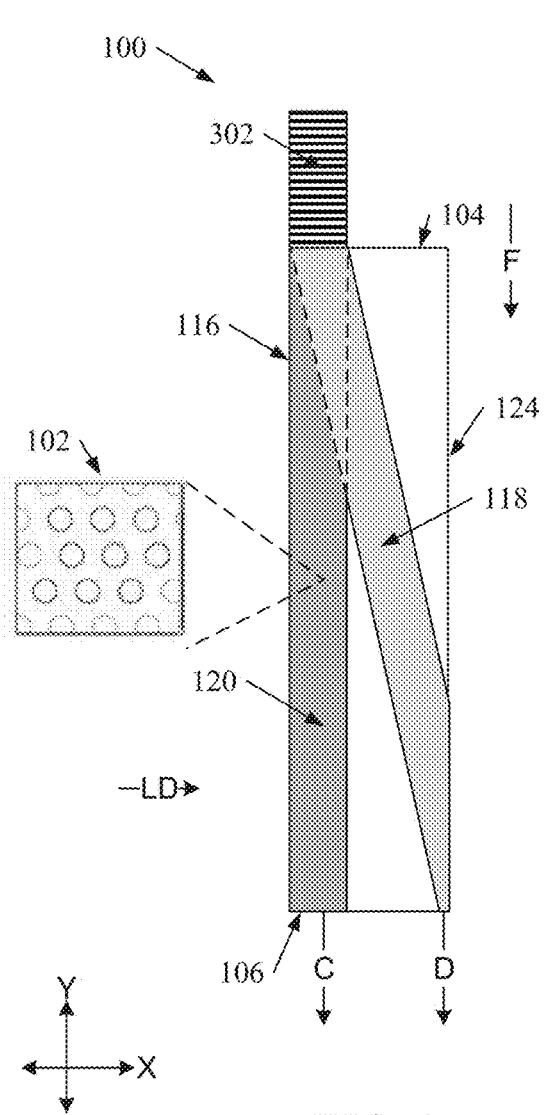
FIG. 3A illustrates a diagram of an example, non-limiting microfluidic channel that can comprise one or more deterministic lateral displacement arrays, which can facilitate screening for mutations such as CNV and/or chromosomal aneuploidy in accordance with one or more embodiments described herein.

FIGS. 3A and/or 3B illustrate diagrams of example, non-limiting microfluidic channels 100 that can comprise one or more nano-DLD arrays 102, which can facilitate screening for one or more mutations, such as CNV and/or chromosomal aneuploidy, through lateral displacement of one or more molecules based on size in accordance with one or more embodiments described herein. Repetitive description of like elements employed in other embodiments described herein is omitted for sake of brevity.

As shown in FIGS. 3A and/or 3B, a fifth sample fluid 302 can be supplied to the one or more microfluidic channels 100 to facilitate screening for mutations such as CNV and/or chromosomal aneuploidy. The fifth sample fluid 302 can be prepared by adding one or more target molecular probes and/or one or more reference molecular probes to one or more genetic materials 210. The one or more genetic materials 210 can be enzymatically and/or mechanically fragmented to a size greater than the critical diameter of the one or more nano-DLD arrays 102. For example, the one or more genetic materials 210 can be fragmented to greater than or equal to 1000 bp and less than or equal to 20,000 bp. The one or more target molecular probes can have an affinity to bond to a target nucleic acid sequence (e.g., defining a target gene and/or target chromosome). Further, the one or more target molecular probes can be smaller than the critical diameter of the one or more nano-DLD arrays 102. For example, the one or more target molecular probes can be greater than or equal to 25 bp and less than or equal to 200 bp. The one or more reference molecular probes can have an affinity to bond to a reference nucleic acid sequence, which can be distinct from the target nucleic acid sequence and/or known to be comprised within the one or more genetic materials 210. Additionally, the one or more target molecular probes and/or the one or more reference molecular probes can be respectively labelled in accordance with one or more embodiments described herein.

Further, the fifth sample fluid 302 can be subject to enzymatic hybridization techniques and/or temperature based hybridization techniques to facilitate hybridizations between the one or more reference molecular probes and the one or more genetic materials 210, and/or potential hybridizations between the one or more target molecular probes and the one or more genetic materials 210. For example, the fifth sample fluid 302 can be annealed to a temperature ranging from, but not limited to, greater than or equal to 50 degrees ° C. and less than or equal to 100° C. (e.g., 95° C.).

In one or more embodiments, exon and/or chromosomal deletion can be detected based on the flow path of the one or more target molecular probes through the one or more nano-DLD arrays 102. For example, if the one or more genetic materials 210 comprise a double deletion of one or more exons and/or chromosomes defined by the target nucleic acid sequence, then the one or more target molecular probes will not hybridize to the one or more genetic materials 210. Further, since the one or more target molecular probes, while unhybridized, are smaller than the critical diameter, the one or more unhybridized target molecular probes can flow through the one or more nano-DLD arrays 102 in a zig-zag path 120. For example, FIG. 3A depicts an exemplary zig-zag path 120 of one or more unhybridized target molecular probes. In contrast, the one or more reference molecular probes, being hybridized to the one or more genetic materials 210 that are larger than the critical diameter of the one or more nano-DLD arrays 102, can flow through the one or more nano-DLD arrays 102 in a bumped path 118. For example, FIG. 3A depicts an exemplary bumped path 118 of the one or more hybridized reference molecular probes. Thus, unhybridized target molecular probes can exit the one or more nano-DLD arrays 102 in a stream (e.g., represented by the "C" arrow) separate from a stream (e.g., represented by the "D" arrow) of the hybridized reference molecular probes.

Figure 3B:
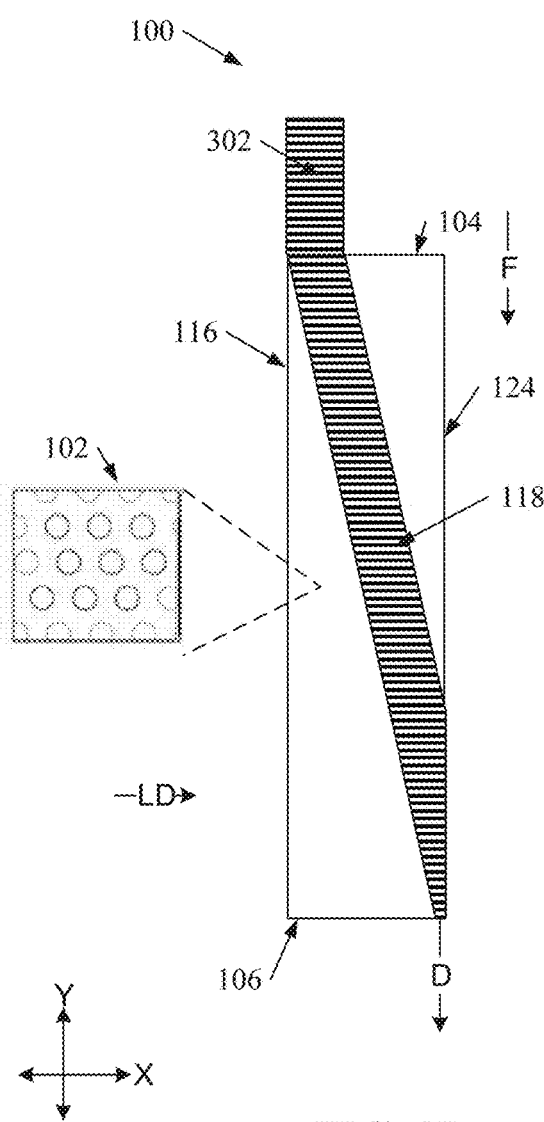
FIG. 3B illustrates a diagram of an example, non-limiting microfluidic channel that can comprise one or more deterministic lateral displacement arrays, which can facilitate screening for one or more mutations such as CNV and/or chromosomal aneuploidy in accordance with one or more embodiments described herein.

However, wherein the one or more target molecular probes flow through the one or more nano-DLD arrays 102 in a bumped path 118 (e.g., as shown in FIG. 3B), that at least some of the target nucleic acid sequence is present to facilitate hybridization of the one or more target molecular probes. Therefore, one or more target molecular probes flowing in a bumped path 118 (e.g., as shown in FIG. 3B) can be indicative that the one or more genetic materials 210 are not subject to double deletion with regards to the target nucleic acid sequences.

Further, in one or more embodiments CNV and/or chromosomal aneuploidy can be detected based on a ratio of bumped target molecular probes to bumped reference molecular probes. For example, single deletion and/or amplification of the one or more target nucleic acid sequences (e.g., target exons and/or chromosomes) based on said ratio. Wherein one or more of the target molecular probes flow in a bumped path 118 the number of bumped (e.g., laterally displaced) target molecular probes can be counted over a period of time and/or the number of bumped (e.g., laterally displaced) reference molecular probes can be counted over the same period of time. Further, a ratio of total bumped target molecular probes to total bumped reference molecular probes can be derived. A ratio equal to one (e.g., 1 target molecular probe: 1 reference molecular probe) can be indicative that the one or more genetic materials 210 do not comprise mutations such as CNV and/or chromosomal aneuploidy. A ratio less than one (e.g., 2 target molecular probe: 3 reference molecular probe) can be indicative that the one or more genetic materials 210 comprises mutations such as CNV and/or chromosomal aneuploidy. For instance, a ratio of less than one can be indicative of single deletion regarding the target nucleic acid sequence (e.g., the target exon and/or chromosome). A ratio greater than one (e.g., 3 target molecular probe: 2 reference molecular probe) can be indicative that the one or more genetic materials 210 comprises mutations such as CNV and/or chromosomal aneuploidy. For instance, a ratio of greater than one can be indicative of amplification regarding the target nucleic acid sequence (e.g., the target exon and/or chromosome). Thus, one or more embodiments described herein can advantageously detect presence of CNVs and/or chromosomal aneuploidy and/or type of CNVs and/or chromosomal aneuploidy.

Figure 4:
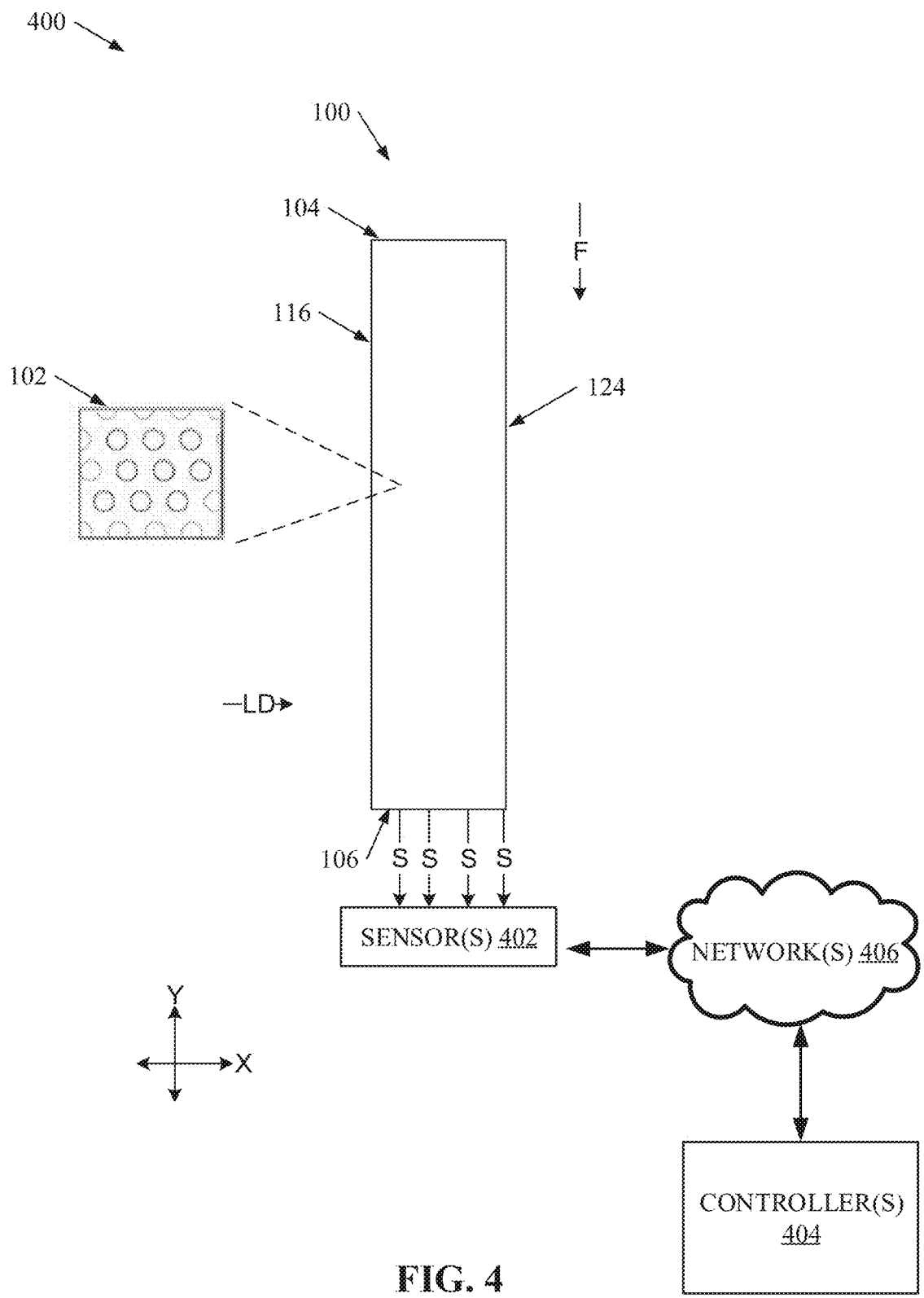
FIG. 4 illustrates a diagram of an example, non-limiting system that can comprise a microfluidic channel and can comprise facilitate screening one or more DNA segments for one or more mutations in accordance with one or more embodiments described herein.

FIG. 4 illustrates a diagram of the example, non-limiting system 400 that can comprise the one or more microfluidic channels 100 and can facilitate screening for one or more mutations in accordance with one or more embodiments described herein. Repetitive description of like elements employed in other embodiments described herein is omitted for sake of brevity. As shown in FIG. 4, in various embodiments the system 400, for example the one or more microfluidic channels 100, can comprise one or more sensors 402, which can be connected to one or more controllers 404 via one or more networks 406.

The system 400 can facilitate any of the various embodiments described herein. For example, the one or more microfluidic channels 100 depicted in FIG. 4 can be any of the microfluidic channels 100 in the various embodiments described herein. In another example, any of the sample fluids described herein (e.g., first sample fluid 108, second sample fluid 110, third sample fluid 112, fourth sample fluid 114, and/or fifth sample fluid 302) can be inputted to the one or more microfluidic channels 100 of FIG. 4 (e.g., via the one or more inlets 104), can traverse the one or more nano-DLD arrays 102 of FIG. 4 in various flow paths (e.g., a bumped path 118, a zig-zag path 120, and/or a partially bumped path 122), and/or can exit the one or more microfluidic channels 100 in one or more streams (e.g., as represented by the one or more "S" arrows).

The one or more sensors 402 can facilitate detection of the one or more molecular probes (e.g., first molecular probe 202, second molecular probe 204, third molecular probe 206, fourth molecular probe 208, target molecular probe, and/or reference molecular probe) as the one or more molecular probes traverse the one or more nano-DLD arrays 102 and/or exit the microfluidic channel 100. While FIG. 4 depicts a sensor 402 positioned downstream (e.g., along the flow direction represented by the "F" arrow) of the one or more outlets 106, the architecture of the one or more microfluidic channels 100 is not so limited. For example, the sensor 402 can be positioned between the one or more inlets 104 and/or the one or more outlets 106. Moreover, the sensor 402 can be positioned adjacent to and/or within the one or more inlets 104 and/or outlets 106. Further, the one or more microfluidic channels 100 can comprise a plurality of sensors 402 at respective locations throughout the one or more microfluidic channels 100 (e.g., between the one or more inlets 104 and the one or more outlets 106, downstream of the one or more outlets 106, and/or adjacent to and/or within the one or more inlets 104 and/or outlets 106).

The one or more sensors 402 can facilitate detection of the location of the one or more molecular probes (e.g., first molecular probe 202, second molecular probe 204, third molecular probe 206, fourth molecular probe 208, target molecular probe, and/or reference molecular probe) as the one or more molecular probes exit the one or more outlets 106 and/or as the one or more molecular probes traverse the one or more nano-DLD arrays 102. The one or more sensors 402 can comprise, but not limited to: biosensors, electrochemical sensors, photosensors, optical light absorption sensors, a combination thereof, and/or the like. The one or more sensors 402 can detect: a position of the one or more molecular probes within the one or more nano-DLD arrays 102, a region of the one or more outlets 106 from which the one or more molecular probes have exited, individual single molecule counts of respective molecular probes and/or molecules comprising the target nucleic acid sequences and/or reference nucleic acid sequences, a combination thereof, and/or the like.

The one or more sensors 402 can be operably coupled to one or more controllers 404 via one or more networks 406. The one or more networks 406 can comprise wired and wireless networks, including, but not limited to, a cellular network, a wide area network (WAN) (e.g., the Internet) or a local area network (LAN). For example, the one or more sensors 402 can communicate with the one or more controllers 404 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Additionally, the one or more networks 406 can comprise and/or be located within a cloud computing environment.

The one or more controllers 404 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 400 (e.g., via use of a LOC comprising the one or more microfluidic channels 100) can utilize the one or more controllers 404 to view and/or analyze one or more detections made by the one or more sensors 402. For example, the one or more sensors 402 can send data (e.g., regarding detections) to the one or more controllers 404 (e.g., via a direct connection and/or via the one or more networks 406). In one or more embodiments, the one or more controllers 404 can determine, based on the detections of the one or more sensors 402, the flow path traversed by the one or more molecules (e.g., molecular probes) through the one or more nano-DLD arrays 102. For example, the one or more controllers 404 can determine whether a subject flow path exhibits lateral displacement towards a collection region and/or whether the a subject flow path exhibits a zig-zag path 120 through the one or more nano-DLD arrays 102 with minimal lateral displacement. Moreover, based on the determined flow path, the one or more controllers 404 can determine whether the one or more genetic materials 210 comprise one or more mutations.

Additionally, the one or more controllers 404 can comprise one or more displays that can present one or more outputs detected by the one or more sensors 402 and/or determined by the one or more controllers 404 (e.g., by one or more processors comprised within the one or more controllers 404) to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

Figure 5:
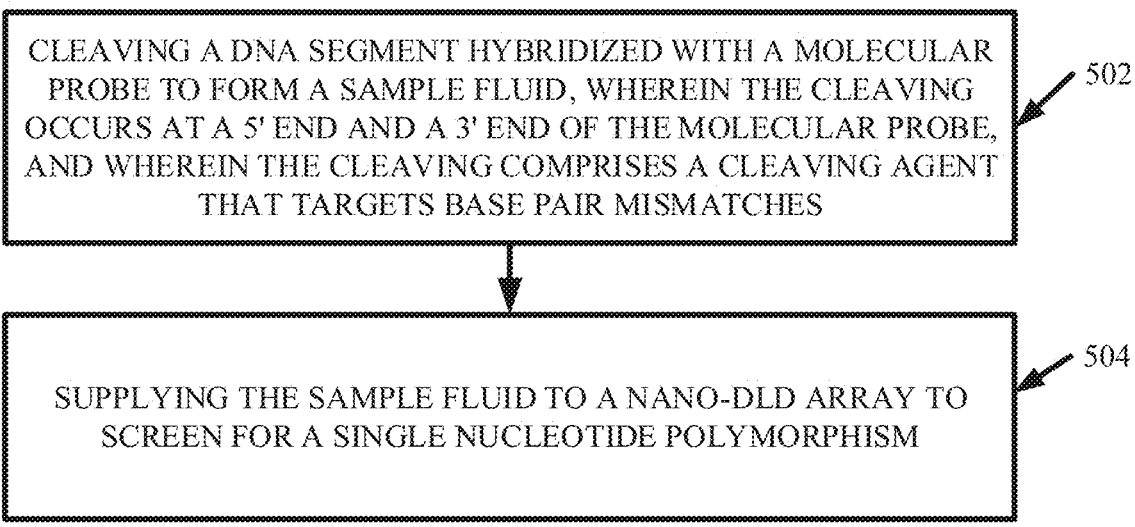
FIG. 5 illustrates a flow diagram of an example, non-limiting method that can facilitate screening for single nucleic polymorphisms using one or more deterministic lateral displacement arrays in accordance with one or more embodiments described herein.

FIG. 5 illustrates a flow diagram of an example, non-limiting method 500 that can facilitate screening for one or more mutations, such as SNPs, through the use one or more microfluidic channels 100 in accordance with one or more embodiments described herein. Repetitive description of like elements employed in other embodiments described herein is omitted for sake of brevity.

At 502, the method 500 can comprise cleaving a DNA segment hybridized with one or more molecular probes (e.g., first molecular probe 202, second molecular probe 204, third molecular probe 206, and/or fourth molecular probe 208) to form one or more sample fluids (e.g., first sample fluid 108, second sample fluid 110, third sample fluid 112, and/or fourth sample fluid 114). The cleaving can occur at a 5' end and/or a 3' end of the molecular probes. Additionally, the cleaving (e.g., site-specific cleaving) can comprise a cleaving agent (e.g., a chemical cleaving agent and/or an enzymatic cleaving agent) that can target base pair mismatches (e.g., engineered mismatches and/or non-engineered mismatches).

At 504, the method 500 can comprise supplying the one or more sample fluids to one or more nano-DLD arrays 102 to screen for one or more SNPs. For example, the one or more SNPs can be detected based on a flow path of the one or more molecular probes through the one or more nano-DLD arrays 102. An advantage of method 500 can be that the subject screening for SNPs can be performed much more rapidly than conventional techniques (e.g., at least because the one or more microfluidic channels 100 can be operated on a LOC).

FIG. 6 illustrates a flow diagram of an example, non-limiting method 600 that can facilitate screening for one or more mutations, such as SNPs, through the use one or more microfluidic channels 100 in accordance with one or more embodiments described herein. Repetitive description of like elements employed in other embodiments described herein is omitted for sake of brevity.

At 602, the method 600 can comprise cleaving a DNA segment hybridized with one or more molecular probes (e.g., first molecular probe 202, second molecular probe 204, third molecular probe 206, and/or fourth molecular probe 208) to form one or more sample fluids (e.g., first sample fluid 108, second sample fluid 110, third sample fluid 112, and/or fourth sample fluid 114). The cleaving can occur at a 5' end and/or a 3' end of the molecular probes. Additionally, the cleaving (e.g., site-specific cleaving) can comprise a cleaving agent (e.g., a chemical cleaving agent and/or an enzymatic cleaving agent) that can target base pair mismatches (e.g., engineered mismatches and/or non-engineered mismatches).

At 604, the method 600 can comprise supplying the one or more sample fluids to one or more nano-DLD arrays 102 to screen for one or more SNPs. For example, the one or more SNPs can be detected based on a flow path of the one or more molecular probes through the one or more nano-DLD arrays 102. For instance, depending of the presence of one or more SNPs within the one or more DNA segments, the method 600 can proceed to 606 or 608.

Wherein the one or more molecular probes are hybridized to respective portions of the DNA segment that do not comprise a SNP, the method can proceed to 606. At 606, the one or more molecular probes can remain intact between the 5' end and/or the 3' end subsequent to the cleaving at 602 (e.g., in accordance with the first cleaving scheme 212 and/or the second cleaving scheme 214). Further, the one or more molecular probes can flow through the one or more nano-DLD arrays 102 in a bumped path 118 (e.g., at least because the one or more intact molecular probes are larger than the critical diameter of the one or more nano-DLD arrays 102). The bumped path 118 of the one or more molecular probes can indicate that the one or more DNA segments do not comprise a SNP at the one or more portions hybridized to the one or more molecular probes.

Wherein the one or more molecular probes are hybridized to respective portions of the DNA segment that comprise a SNP, the method can proceed to 608. At 608, the cleaving at 602 can further cleave the one or more molecular probes between the 5' end and/or the 3' end (e.g., at a location corresponding to a non-engineered mismatch caused by a SNP). Further, the one or more molecular probes within the one or more sample fluids can be too small to be laterally displaced by the one or more nano-DLD arrays 102. Thus, the one or more molecular probes can flow through the one or more nano-DLD arrays 102 in a zig-zag path 120; thereby indicating the one or more DNA segments comprise a SNP at the one or more portions hybridized to the one or more molecular probes. An advantage of method 600 can that the subject screening is highly adaptable to various DNA segments.

FIG. 7 illustrates a flow diagram of an example, non-limiting method 700 that can facilitate screening for one or more mutations, such as SNPs, through the use one or more microfluidic channels 100 in accordance with one or more embodiments described herein. Repetitive description of like elements employed in other embodiments described herein is omitted for sake of brevity.

At 702, the method 700 can comprise forming a first sample fluid (e.g., first sample fluid 108, second sample fluid 110, third sample fluid 112, and/or fourth sample fluid 114) by hybridizing a first molecular probe (e.g., first molecular probe 202, second molecular probe 204, third molecular probe 206, and/or fourth molecular probe 208) to a first DNA segment. In one or more embodiments, the forming at 702 can further comprise a site-specific cleaving that targets mismatch pairs between the first molecular probe and the first DNA segment.

At 704, the method 700 can comprising a second sample fluid (e.g., first sample fluid 108, second sample fluid 110, third sample fluid 112, and/or fourth sample fluid 114) by hybridizing a second molecular probe (e.g., first molecular probe 202, second molecular probe 204, third molecular probe 206, and/or fourth molecular probe 208) to a second DNA segment. The first DNA segment and the second DNA segment can be defined by a same nucleic acid sequence. In one or more embodiments, the forming at 704 can further comprise a site-specific cleaving that targets mismatch pairs between the second molecular probe and the second DNA segment.

At 706, the method 700 can comprise screening for a SNP in the same nucleic acid sequence by supplying the first sample fluid to a first nano-DLD array 102 and/or the second sample fluid to a second nano-DLD array 102. In one or more embodiments, detection of a SNP can be determined based on whether the first molecular probe and/or the second molecular probe flow through the respective nano-DLD arrays 102 in a bump path 118 or a zig-zag path 120. Further, wherein an SNP is detected, the location of the SNP can be determined based on which, or both, of the respective molecular probes flow through the respective nano-DLD arrays 102 in a zig-zag path 120. An advantage of method 700 can be that the subject screening is able to detect one or more SNPs and/or determine the location of one or more SNPs rapidly and/or efficiently.

FIG. 8 illustrates a flow diagram of an example, non-limiting method 800 that can facilitate screening for one or more mutations, such as SNPs, through the use one or more microfluidic channels 100 in accordance with one or more embodiments described herein. Repetitive description of like elements employed in other embodiments described herein is omitted for sake of brevity.

At 802, the method 800 can comprise forming a first sample fluid (e.g., first sample fluid 108, second sample fluid 110, third sample fluid 112, and/or fourth sample fluid 114) by hybridizing a first molecular probe (e.g., first molecular probe 202, second molecular probe 204, third molecular probe 206, and/or fourth molecular probe 208) to a first DNA segment. Further, the forming at 802 can also comprise cleaving the first DNA segment at a 5' and/or a 3' end of the first molecular probe using a cleaving agent that can target base pair mismatches.

At 804, the method 800 can comprising a second sample fluid (e.g., first sample fluid 108, second sample fluid 110, third sample fluid 112, and/or fourth sample fluid 114) by hybridizing a second molecular probe (e.g., first molecular probe 202, second molecular probe 204, third molecular probe 206, and/or fourth molecular probe 208) to a second DNA segment. The first DNA segment and the second DNA segment can be defined by a same nucleic acid sequence. Further, the forming at 804 can also comprise cleaving the second DNA segment at a 5' and/or a 3' end of the second molecular probe using a cleaving agent that can target base pair mismatches.

At 806, the method 800 can comprise screening for a SNP in the same nucleic acid sequence by supplying the first sample fluid to a first nano-DLD array 102 and/or the second sample fluid to a second nano-DLD array 102. In one or more embodiments, detection of a SNP can be determined based on whether the first molecular probe and/or the second molecular probe flow through the respective nano-DLD arrays 102 in a bump path 118 or a zig-zag path 120. Further, wherein an SNP is detected, the location of the SNP can be determined based on which, or both, of the respective molecular probes flow through the respective nano-DLD arrays 102 in a zig-zag path 120.

Wherein a first portion (e.g., hybridized to the first molecular probe) of the same nucleic acid sequence remains intact subsequent to the cleaving of the first DNA segment and/or a second portion (e.g., hybridized to the second molecular probe) of the same nucleic acid sequence remains intact subsequent to the cleaving of the second DNA segment, the method can proceed to 808. At 808 the first molecular probe can flow through the first nano-DLD array 102 in a first bumped path 118. Also, the second molecular probe can flow through the second nano-DLD array 102 in a second bumped path 118. The bumped paths 118 of the first molecular probe and/or the second molecular probe can indicate that the first portion of the DNA segments (e.g., hybridized to the first molecular probe) and/or the second portion of the DNA segments (e.g., hybridized to the second molecular probe) do not comprise SNPs.

Wherein a first portion (e.g., hybridized to the first molecular probe) of the same nucleic acid sequence remains intact subsequent to the cleaving of the first DNA segment, but the cleaving at 804 further comprises cleaving the second DNA segment between the 5' end and/or the 3' end of the second molecular probe, the method can proceed to 810. At 810 the first molecular probe can flow through the first nano-DLD array 102 in a bumped path 118. Also, the second molecular probe can flow through the second nano-DLD array 102 in a zig-zag path 120. The zig-zag path 120 path of the second molecular can indicate that a SNP is comprised within a portion of the same nucleic acid sequence hybridized to the second molecular probe.

Wherein the cleaving at 802 further comprises cleaving the first DNA segment between the 5' end and/or the 3' end of the first molecular probe and/or the cleaving at 804 further comprises cleaving the second DNA segment between the 5' end and/or the 3' end of the second molecular probe, the method can proceed to 812. At 812 the first molecular probe can flow through the first nano-DLD array 102 in a first zig-zag path 120. Also, the second molecular probe can flow through the second nano-DLD array 102 in a second zig-zag path 120. The zig-zag paths 120 of the first molecular probe and/or the second molecular probe can indicate that the same nucleic acid sequence comprise a SNP at a portion subject to the bonding affinity of both the first molecular probe and the second molecular probe. Thus, method 800 can advantageously locate specific positions of one or more detected SNPs.

FIG. 9 illustrates a flow diagram of an example, non-limiting method 900 that can facilitate screening for one or more mutations, such as CVNs and/or chromosomal aneuploidy, through the use one or more microfluidic channels 100 in accordance with one or more embodiments described herein. Repetitive description of like elements employed in other embodiments described herein is omitted for sake of brevity.

At 902, the method 900 can comprise adding one or more first molecular probes (e.g., one or more target molecular probes) to a sample of genetic material (e.g., genetic material 210). The first molecular probe can have an affinity to bod to a target nucleic acid sequence.

At 904, the method 900 can comprise hybridizing one or more second molecular probes (e.g., one or more reference molecular probes) to one or more reference nucleic acid sequences comprised within the sample of genetic material.

At 906, the method 900 can comprise screening for a mutation (CVNs and/or chromosomal aneuploidy) in the sample of genetic material by supplying the sample of genetic material to one or more nano-DLD arrays 102. Additionally, the one or more first molecular probes can be smaller than a critical diameter for lateral displacement by the one or more nano-DLD arrays 102. The method 900 can facilitate detection of mutations such as CVNs and/or chromosomal aneuploidy by analyzing the flow path of the one or more first molecular probes through the one or more nano-DLD arrays 102 and/or by determining a ratio of first molecular probes bumped by the one or more nano-DLD arrays 102 to second molecular probes bumped by the one or more nano-DLD arrays 102. As compared to conventional techniques, an advantage of method 900 be the rapid and accurate screening of mutations such as CVNs and/or chromosomal aneuploidy.

FIG. 10 illustrates a flow diagram of an example, non-limiting method 1000 that can facilitate screening for one or more mutations, such as CVNs and/or chromosomal aneuploidy, through the use one or more microfluidic channels 100 in accordance with one or more embodiments described herein. Repetitive description of like elements employed in other embodiments described herein is omitted for sake of brevity.

At 1002, the method 1000 can comprise adding one or more first molecular probes (e.g., one or more target molecular probes) to a sample of genetic material (e.g., genetic material 210). The first molecular probe can have an affinity to bod to a target nucleic acid sequence.

At 1004, the method 1000 can comprise hybridizing one or more second molecular probes (e.g., one or more reference molecular probes) to one or more reference nucleic acid sequences comprised within the sample of genetic material.

At 1006, the method 1000 can comprise screening for a mutation (CVNs and/or chromosomal aneuploidy) in the sample of genetic material by supplying the sample of genetic material to one or more nano-DLD arrays 102. Additionally, the one or more first molecular probes can be smaller than a critical diameter for lateral displacement by the one or more nano-DLD arrays 102.

In one or more embodiments, the method 1000 can further proceed to 1008 and can further comprise determining that the sample of genetic material comprises the mutation based on the one or more first molecular probes flowing through the one or more nano-DLD arrays 102 in a zig-zag path 120. For example, the one or more first molecular probes flowing in the zig-zag path 120 can be indicative of a deletion of one or more target nucleic acid sequence (e.g., a double deletion of one or more target exons and/or target chromosomes).

Wherein the one or more first molecular probes and/or the one or more second molecular probes can flow through the one or more nano-DLD arrays 102 in a bumped path 118, the method 1000 can further proceed to 1010. At 1010 the method 1000 can comprise determining a ratio of a first amount of the first molecular probe flowing through the bumped path 118 to a second amount of the second molecular probe flowing through the bumped path. Additionally, the method 1000 can comprise determining whether the sample of genetic material comprises the mutation (e.g., CVNs and/or chromosomal aneuploidy) based on the ratio.

Figure 11:
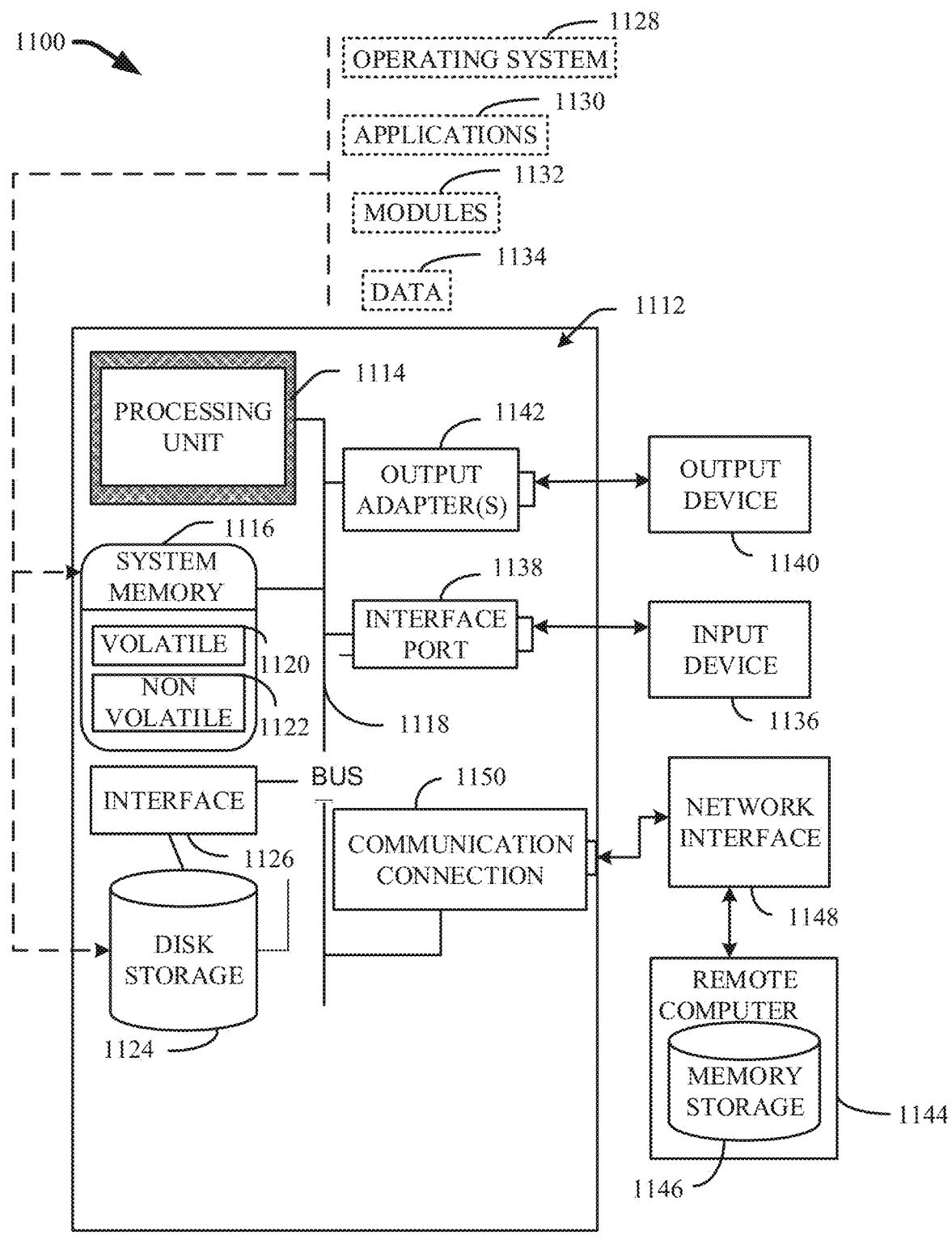
FIG. 11 illustrates a block diagram of an example, non-limiting operating environment in which one or more embodiments described herein can be facilitated.

In order to provide a context for the various aspects of the disclosed subject matter, FIG. 11 as well as the following discussion are intended to provide a general description of a suitable environment in which the various aspects of the disclosed subject matter can be implemented. FIG. 11 illustrates a block diagram of an example, non-limiting operating environment 1100 in which one or more embodiments described herein can be facilitated. For example, the operating environment 1100 can comprise and/or otherwise facilitate one or more features of the one or more controllers 404 described herein in accordance with one or more embodiments. Repetitive description of like elements employed in other embodiments described herein is omitted for sake of brevity. With reference to FIG. 11, a suitable operating environment 1100 for implementing various aspects of this disclosure can include a computer 1112. The computer 1112 can also include a processing unit 1114, a system memory 1116, and a system bus 1118. The system bus 1118 can operably couple system components including, but not limited to, the system memory 1116 to the processing unit 1114. The processing unit 1114 can be any of various available processors. Dual microprocessors and other multiprocessor architectures also can be employed as the processing unit 1114. The system bus 1118 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1116 can also include volatile memory 1120 and nonvolatile memory 1122. The basic input/output system (BIOS), containing the basic routines to transfer information between elements within the computer 1112, such as during start-up, can be stored in nonvolatile memory 1122. By way of illustration, and not limitation, nonvolatile memory 1122 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1120 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1112 can also include removable/non-removable, volatile/non-volatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1124 to the system bus 1118, a removable or non-removable interface can be used, such as interface 1126. FIG. 11 also depicts software that can act as an intermediary between users and the basic computer resources described in the suitable operating environment 1100. Such software can also include, for example, an operating system 1128. Operating system 1128, which can be stored on disk storage 1124, acts to control and allocate resources of the computer 1112. System applications 1130 can take advantage of the management of resources by operating system 1128 through program modules 1132 and program data 1134, e.g., stored either in system memory 1116 or on disk storage 1124. It is to be appreciated that this disclosure can be implemented with various operating systems or combinations of operating systems. A user enters commands or information into the computer 1112 through one or more input devices 1136. Input devices 1136 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1114 through the system bus 1118 via one or more interface ports 1138. The one or more Interface ports 1138 can include, for example, a serial port, a parallel port, a game port, and a universal serial bus (USB). One or more output devices 1140 can use some of the same type of ports as input device 1136. Thus, for example, a USB port can be used to provide input to computer 1112, and to output information from computer 1112 to an output device 1140. Output adapter 1142 can be provided to illustrate that there are some output devices 1140 like monitors, speakers, and printers, among other output devices 1140, which require special adapters. The output adapters 1142 can include, by way of illustration and not limitation, video and sound cards that provide a means of connection between the output device 1140 and the system bus 1118. It should be noted that other devices and/or systems of devices provide both input and output capabilities such as one or more remote computers 1144.

Computer 1112 can operate in a networked environment using logical connections to one or more remote computers, such as remote computer 1144. The remote computer 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer 1144. Remote computer 1144 can be logically connected to computer 1112 through a network interface 1148 and then physically connected via communication connection 1150. Further, operation can be distributed across multiple (local and remote) systems. Network interface 1148 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
cleaving a deoxyribonucleic acid segment hybridized with a molecular probe to form a sample fluid, wherein the cleaving occurs at a first end of the molecular probe and a second end of the molecular probe, wherein the sample fluid has a plurality of base pair mismatches with respect to the deoxyribonucleic acid segment and the molecular probe, wherein a first base pair mismatch from the plurality of base pair mismatches is located at the first end of the molecular probe and a second base pair mismatch from the plurality of the base pair mismatches is located at the second end of the molecular probe, and wherein the cleaving comprises a cleaving agent that targets base pair mismatches with respect to the deoxyribonucleic acid segment and the molecular probe, wherein the base pair mismatches include the plurality of base pair mismatches;
supplying the sample fluid to a nanoscale deterministic lateral displacement array to screen for a single nucleotide polymorphism; and
determining whether the deoxyribonucleic acid segment comprises the single nucleotide polymorphism at a position between the first base pair mismatch and the second base pair mismatch based on a flow path of the molecular probe through the nanoscale deterministic lateral displacement array.

2. The method of claim 1, wherein the molecular probe remains intact between the first end of the molecular probe and the second end of the molecular probe subsequent to the cleaving, and wherein the molecular probe flows through the nanoscale deterministic lateral displacement array in a bumped path.

3. The method of claim 1, wherein a third base pair mismatch from the plurality of base pair mismatches is located between the first base pair mismatch and the second base pair mismatch, wherein the cleaving further cleaves the molecular probe between the first end of the molecular probe and the second end of the molecular probe, and wherein the molecular probe within the sample fluid is too small to be laterally displaced by the nanoscale deterministic lateral displacement array.

4. The method of claim 1, further comprising:
detecting a location of the molecular probe; and
determining the flow path based on the location.

5. The method of claim 1, wherein the molecular probe comprises an identifier selected from a group consisting of a fluorescent tag and a magnetic bead.

6. The method of claim 1, wherein the cleaving agent is selected from a group consisting of a chemical cleaving agent and an enzymatic cleaving agent.

7. The method of claim 6, wherein the cleaving agent is selected from a second group consisting of piperidine and endonucleases.

8. The method of claim 1, comprising:
forming a second sample fluid by cleaving a second deoxyribonucleic acid segment hybridized to a second molecular probe, wherein the deoxyribonucleic acid segment and the second deoxyribonucleic acid segment are defined by a same nucleic acid sequence, wherein the cleaving occurs at a first end of the second molecular probe and a second end of the second molecular probe, wherein the second sample fluid has a second plurality of base pair mismatches with respect to the second deoxyribonucleic acid segment and the second molecular probe, wherein a first base pair mismatch from the second plurality of base pair mismatches is located at the first end of the second molecular probe and a second base pair mismatch from the second plurality of the base pair mismatches is located at the second end of the second molecular probe, and wherein the forming comprises a second cleaving agent that targets the second plurality of base pair mismatches; and screening for the single nucleotide polymorphism in the same nucleic acid sequence by supplying the second sample fluid to a second nanoscale deterministic lateral displacement array.

9. The method of claim 8, wherein the molecular probe is hybridized to a first portion of the same nucleic acid sequence, wherein the second molecular probe is hybridized to a second portion of the same nucleic acid sequence, and wherein the first portion of the same nucleic acid sequence overlaps the second portion of the same nucleic acid sequence.

10. The method of claim 9, wherein the molecular probe remains intact subsequent to the cleaving of the deoxyribonucleic acid segment, wherein the second molecular probe remains intact subsequent to the cleaving of the second deoxyribonucleic acid segment, wherein the molecular probe flows through the nanoscale deterministic lateral displacement array in a first bumped path, and wherein the second molecular probe flows through the second nanoscale deterministic lateral displacement array in a second bumped path.

11. The method of claim 9, wherein the molecular probe remains intact subsequent to the cleaving of the deoxyribonucleic acid segment, wherein the cleaving of the second deoxyribonucleic acid segment further comprises cleaving the second molecular probe between first end of the second molecular probe and the second end of the second molecular probe, wherein a third base pair mismatch from the second plurality of base pair mismatches is located between the first base pair mismatch from the second plurality of base pair mismatches and the second base pair mismatch from the second plurality of base pair mismatches, wherein the molecular probe flows through the nanoscale deterministic lateral displacement array in a bumped path, and wherein the second molecular probe flows through the second nanoscale deterministic lateral displacement array in a zig-zag path.

12. The method of claim 9, wherein the cleaving of the deoxyribonucleic acid segment further comprises cleaving the molecular probe between first end of the molecular probe and the second end of the molecular probe, wherein a third base pair mismatch from the plurality of base pair mismatches is located between the first base pair mismatch from the plurality of base pair mismatches and the second base pair mismatch from the plurality of base pair mismatches, wherein the cleaving of the second deoxyribonucleic acid segment further comprises cleaving the second molecular probe between first end of the second molecular probe and the second end of the second molecular probe, wherein a third base pair mismatch from the second plurality of base pair mismatches is located between the first base pair mismatch from the second plurality of base pair mismatches and the second base pair mismatch from the second plurality of base pair mismatches, wherein the molecular probe flows through the nanoscale deterministic lateral displacement array in a first zig-zag path, and wherein the second molecular probe flows through the second nanoscale deterministic lateral displacement array in a second zig-zag path.

13. The method of claim 9, wherein the molecular probe comprises a first identifier selected from a first group consisting of a fluorescent tag and a magnetic bead, wherein the second molecular probe comprises a second identifier selected from a second group consisting of the fluorescent tag and the magnetic bead, and wherein the first cleaving agent is selected from a third group consisting of a first chemical cleaving agent and a first enzymatic cleaving agent, and wherein the second cleaving agent is selected from a fourth group consisting of a second chemical cleaving agent and a second enzymatic cleaving agent.

* * * * *